US009364016B2

(12) United States Patent
Kannar et al.

(10) Patent No.: US 9,364,016 B2
(45) Date of Patent: Jun. 14, 2016

(54) EXTRACTS DERIVED FROM SUGAR CANE AND A PROCESS FOR THEIR MANUFACTURE

(75) Inventors: David Kannar, Belgrave South (AU); Barry James Kitchen, Bon Beach (AU)

(73) Assignee: The Product Makers (Australia) Pty Ltd, Victoria (AU)

( * ) Notice: Subject to any disclaimer, the term of this patent is extended or adjusted under 35 U.S.C. 154(b) by 592 days.

(21) Appl. No.: 12/440,717

(22) PCT Filed: Sep. 19, 2007

(86) PCT No.: PCT/AU2007/001382
§ 371 (c)(1),
(2), (4) Date: Apr. 21, 2009

(87) PCT Pub. No.: WO2008/034180
PCT Pub. Date: Mar. 27, 2008

(65) Prior Publication Data
US 2010/0004185 A1  Jan. 7, 2010

(30) Foreign Application Priority Data
Sep. 19, 2006 (AU) ................. 2006905179

(51) Int. Cl.
*A23L 1/09* (2006.01)
*C13K 13/00* (2006.01)
*A23L 1/30* (2006.01)

(52) U.S. Cl.
CPC .................... *A23L 1/3002* (2013.01)

(58) Field of Classification Search
CPC ...... A23L 1/3002; C13B 20/165; C13B 35/08
USPC ........ 426/618, 639, 655, 658; 514/23; 127/42
See application file for complete search history.

(56) References Cited

U.S. PATENT DOCUMENTS

| | | | |
|---|---|---|---|
| 2,170,713 A | 8/1939 | Fattinger | |
| 3,619,293 A * | 11/1971 | Niimi et al. | 127/30 |
| 3,975,205 A | 8/1976 | Munir et al. | |
| 4,101,338 A | 7/1978 | Rapaport et al. | |
| 4,111,714 A | 9/1978 | Hippchen et al. | |
| 4,116,712 A | 9/1978 | Othmer | |
| 4,333,770 A | 6/1982 | Neuzil et al. | |
| 4,359,430 A | 11/1982 | Heikkila et al. | |
| 4,404,037 A | 9/1983 | Broughton | |
| 4,523,959 A | 6/1985 | Exertier | |
| 4,523,999 A | 6/1985 | Toyoshi et al. | |
| 5,096,594 A | 3/1992 | Rabinowitz | |
| 5,127,957 A | 7/1992 | Heikkila et al. | |
| 5,382,294 A | 1/1995 | Rimedio et al. | |
| 5,384,035 A | 1/1995 | Smolnik et al. | |
| 5,454,875 A | 10/1995 | Clarke | |
| 5,482,631 A | 1/1996 | Saska et al. | |
| 5,556,546 A | 9/1996 | Tanimura et al. | |
| 5,955,269 A * | 9/1999 | Ghai et al. | 435/6.11 |
| 6,093,326 A | 7/2000 | Heikkila et al. | |
| 6,099,654 A | 8/2000 | Kaneko et al. | |
| 6,217,664 B1 | 4/2001 | Baniel | |
| 6,372,049 B1 | 4/2002 | Shimanskaya et al. | |
| 6,406,547 B1 | 6/2002 | Donovan et al. | |
| 6,406,548 B1 * | 6/2002 | Donovan et al. | 127/55 |
| 6,475,390 B1 | 11/2002 | Durham et al. | |
| 6,528,099 B1 | 3/2003 | Garti et al. | |
| 6,723,369 B2 | 4/2004 | Burgess | |
| 6,869,625 B2 | 3/2005 | Gupta et al. | |
| 7,015,339 B2 | 3/2006 | Khare et al. | |
| 7,312,199 B2 | 12/2007 | Burdick et al. | |
| 8,138,162 B2 * | 3/2012 | Kannar | A23L 1/09 127/42 |
| 2001/0001178 A1 * | 5/2001 | Donovan et al. | 127/55 |
| 2001/0001956 A1 | 5/2001 | Hyoky et al. | |
| 2002/0150652 A1 | 10/2002 | Antila et al. | |
| 2002/0169311 A1 | 11/2002 | Paananen et al. | |
| 2002/0187219 A1 | 12/2002 | Yang et al. | |
| 2003/0124170 A1 | 7/2003 | Gallaher et al. | |
| 2003/0124208 A1 | 7/2003 | Makino et al. | |
| 2003/0147978 A1 * | 8/2003 | Araki et al. | 424/750 |
| 2003/0161903 A1 | 8/2003 | Konishi et al. | |
| 2003/0165574 A1 | 9/2003 | Ward et al. | |
| 2003/0198694 A1 | 10/2003 | Chou | |
| 2003/0232763 A1 | 12/2003 | Jia | |
| 2004/0001862 A1 | 1/2004 | Xiu | |
| 2004/0006222 A1 | 1/2004 | Paananen et al. | |
| 2004/0006223 A1 | 1/2004 | Karki et al. | |
| 2004/0052915 A1 * | 3/2004 | Carlson et al. | 426/548 |
| 2004/0060868 A1 | 4/2004 | Heikkila et al. | |
| 2004/0081734 A1 | 4/2004 | Lang | |

(Continued)

FOREIGN PATENT DOCUMENTS

| | | |
|---|---|---|
| CA | 2053412 | 4/1992 |
| CN | 1484974 | 3/2004 |

(Continued)

OTHER PUBLICATIONS

Kannar et al. WO 2005/117608. Mar. 6, 2004.*
Altukhov et al., 2004, Human Physiol. 30(2):216-223.
Anderson, 2008, Proc. Nutrition Soc. 67:48-53.
Baba et al., 2005, Eur. J. Nutr. 44:1-9.
Badescu et al., 2005, Rom. J. Physiol. 42:1-4.
Balasubramanian et al., 2010, Carcinogenesis 31(3):496-503.
Banini et al., 2006, Nutrition 22:1137-1145.
Basu et al., 2010, J. Nutr. 140:1582-1587.
Bento et al., 1998, Carbohydrate Polymers 37:257-261.
Bento et al., 1997, Intl. Sugar J. 99(1187 Suppl.):555-562.
Bento et al., 1997, SIT Poster #722 Publ. Techn. Papers Proc. Ann. Meet. Sugar Industry Technologiests 56:383-392 "Gel Permeation Chromatography of Sugar Materials Using . . . "
Berhow et al., 2000, Mutation Res. 448:11-22.

(Continued)

*Primary Examiner* — Nikki H Dees
(74) *Attorney, Agent, or Firm* — Myers Bigel & Sibley, P.A.

(57) ABSTRACT

An extract derived from sugar cane having GI or burn rate reducing characteristics wherein the extract comprises a mixture of one or more polyphenols, one or more carbohydrates, one or more minerals and one or more organic acids.

12 Claims, 24 Drawing Sheets

(56) References Cited

U.S. PATENT DOCUMENTS

| | | | |
|---|---|---|---|
| 2004/0097429 A1 | 5/2004 | Nieuwenhuizen et al. | |
| 2004/0131749 A1 | 7/2004 | Grabiel et al. | |
| 2004/0151815 A1 | 8/2004 | Jensen et al. | |
| 2004/0191336 A1 | 9/2004 | Hilaly et al. | |
| 2004/0197380 A1 | 10/2004 | Wolf et al. | |
| 2005/0175674 A1 | 8/2005 | Lang et al. | |
| 2005/0181074 A1 | 8/2005 | Watson et al. | |
| 2006/0003029 A1 | 1/2006 | Nash et al. | |
| 2006/0121158 A1 | 6/2006 | Ferruzzi et al. | |
| 2006/0147556 A1 | 7/2006 | Brewer | |
| 2007/0158269 A1 | 7/2007 | Paananen et al. | |
| 2007/0160698 A1 | 7/2007 | Waga et al. | |
| 2007/0178175 A1 | 8/2007 | Matsubara et al. | |
| 2008/0286254 A1 | 11/2008 | Sakamoto et al. | |
| 2009/0047368 A1 | 2/2009 | Numata et al. | |
| 2009/0053333 A1 | 2/2009 | Sambanthamurthi et al. | |
| 2009/0281057 A1 | 11/2009 | Bhaskaran et al. | |
| 2010/0112099 A1 | 5/2010 | Tripp et al. | |
| 2010/0130422 A1 | 5/2010 | Bernaert et al. | |
| 2010/0166851 A1 | 7/2010 | Dallas | |
| 2010/0184666 A1 | 7/2010 | Bernaert et al. | |
| 2014/0315993 A1* | 10/2014 | Kannar .................... A23L 1/09 514/456 |

FOREIGN PATENT DOCUMENTS

| | | |
|---|---|---|
| CN | 1685929 | 10/2005 |
| CN | 101317850 | 12/2008 |
| EP | 1466609 | 10/2004 |
| FR | 2929852 | 10/2009 |
| JP | 53-059044 | 5/1978 |
| JP | 61-69727 | 4/1986 |
| JP | 61-139400 | 6/1986 |
| JP | 61-265068 | 11/1986 |
| JP | 61-268200 | 11/1986 |
| JP | 62-126951 | 6/1987 |
| JP | 63-207400 | 8/1988 |
| JP | 1244000 | 9/1989 |
| JP | 02-020300 | 1/1990 |
| JP | 03-145424 | 6/1991 |
| JP | 04-320691 | 11/1992 |
| JP | 05-211900 | 8/1993 |
| JP | 09-025290 | 1/1997 |
| JP | 11-075758 | 3/1999 |
| JP | 2001-131080 | 5/2001 |
| JP | 2001-200250 | 7/2001 |
| JP | 2001-302533 | 10/2001 |
| JP | 2002-020306 | 1/2002 |
| JP | 2002-161046 | 6/2002 |
| JP | 2003-63975 | 3/2003 |
| JP | 2003-137803 | 5/2003 |
| JP | 2004-065018 | 3/2004 |
| JP | 2004-75612 | 3/2004 |
| JP | 2005-278407 | 10/2005 |
| JP | 2006-131578 | 5/2006 |
| JP | 2006-321772 | 11/2006 |
| JP | 2007-043940 | 2/2007 |
| JP | 2007/063221 | 3/2007 |
| JP | 2008-044872 | 2/2008 |
| JP | 2008-222656 | 9/2008 |
| JP | 2009-298769 | 12/2009 |
| KR | 100894911 | 4/2009 |
| KR | 20090063794 | 6/2009 |
| RU | 2048847 | 11/1995 |
| WO | WO 89/01295 | 3/1988 |
| WO | WO 94/12057 | 6/1994 |
| WO | WO 9749734 | 12/1997 |
| WO | WO 0136690 | 5/2001 |
| WO | WO 01/78629 | 10/2001 |
| WO | WO 02/14477 | 2/2002 |
| WO | WO 03/074144 | 9/2003 |
| WO | WO 03/074145 | 9/2003 |
| WO | WO 03075685 | 9/2003 |
| WO | WO 03099309 | 12/2003 |
| WO | WO 2005/052195 | 6/2005 |
| WO | WO 2005/089066 | 9/2005 |
| WO | WO 2005/105852 | 11/2005 |
| WO | WO 2005117608 | 12/2005 |
| WO | WO 2006/014028 | 2/2006 |
| WO | WO 2006/052007 | 5/2006 |
| WO | WO 2007/041817 | 4/2007 |
| WO | WO 2008/142178 | 11/2008 |
| WO | WO 98/55658 | 4/2009 |
| WO | WO 2009/046492 | 4/2009 |
| WO | WO 2009/136219 | 11/2009 |
| WO | WO 2010/094860 | 8/2010 |
| WO | WO 2010/118474 | 10/2010 |

OTHER PUBLICATIONS

Brown et al., 2009, Br. J. Nutr. 101:886-894.
Burkon et al., 2008, Mol. Nutr. Food Res. 52:549-557.
Chajuss, 2004, "Soy Molasses: Processing and Utilization as a Functional Food," In: Soybeans as Functional Foods and Ingredients, Liu et al., Eds.
Clarke et al., "Polyfructose: A New Microbial Polysaccharide," In: Carbohydrates as Organic Raw Materials, Lichtenthaler, Ed., VCH, Weinheim, 1990.
Coca et al., 2005, Chemosphere 60:1408-1415.
Dal-Pan et al., 2010, BMC Physiol. 10:11.
Dallas et al., 2008, Phytomedicine 15:783-792.
Edye et al., 1998, "The Fate of Soluble Sugarcane Polysaccharides in Sugar Manufacture," Poster.
Fernandes et al., 2009, Talanta 79:222-228.
Frank et al., 2009, J. Nutr. 139:58-62.
Fujita et al., 2000, Abstract AGFD-086, Book of Abstracts, 219th ACS National Meeting, San Francisco, CA, Amer. Chem. Soc., Washington, DC.
Fukino et al., 2008, Eur. J. Clin. Nutr. 62:953-960.
Fukino et al., 2005, J. Nutr. Sci. Vitaminol. 51:335-342.
Hangyal, 1969, Cukoripar 22(5):183-186 (Abstract only; HCAPLUS database record No. 1970:123241).
Hatano et al., 2008, Chemosphere 71:1730-1737.
Hollis et al., 2009, J. Amer. Coll. Nutr. 28(5):574-582.
Islam, 2008, Z. Naturforsch. 63c:233-240.
Jacome et al., 2009, Alim. Nutr. 20(2):185-190.
Kantachote, 2009, Electr. J. Biotechnol. 12(3):12.
Khan et al., 2010, 61(15):4185-4196.
Kita et al., 2004, BioFactors 22:259-263.
Kovacs et al., 2004, Br. J. Nutr. 91:431-437.
Loke et al., 2010, Arterioscler. Thromb. Vasc. Biol. 30:749-757.
Machowetz et al., 2008, Horm. Metab. Res. 40:697-701.
Mantovani et al., 2008, Nutrition 24:305-313.
Mantovani et al., 2006, Cancer Epidemiol. Biomarkers Prev. 15:1030-1034.
Mantovani et al., 2004, Cancer Epidemiol. Biomarkers Prev. 13 (10):1651-1659.
Nagasako-Akazome et al., 2007, J. Oleo Sci. 56(8):417-428.
Ochiai et al., 2009, Hypertension Res. 32:969-974.
Olthof et al., 2000, "Metabolism of Chlorogenic Acid, Querctein-3-rutinoside and . . . " In: Spec. Publ. Royal Soc. Chem: 255 Dietary Anticarcinogens and Antimutagens, pp. 73-75.
Onimawo et al., 2010, African J. Food Agric. Nutr. Develop. 10(5).
Plafi et al., 2009, J. Nutr. Biochem. 20:418-425.
Pena et al., 2003, Chemosphere 51:893-900.
Qu et al., 2007, J. Clin. Rehabil. Tiss. Eng. Res. 11(43):8805-8808.
Schoen et al., 2009, Nutrition 25:499-505.
Shore et al., 1984, Sugar Technol. Rev. 12:1-99.
Simonetti et al., 2001, Meth. Enzymol. 335:122-130.
Stracke et al., 2010, Eur. J. Nutr. 49:301-310.
Tominaga et al., 2006, J. Health Sci. 52(6):672-683.
Vercellotti et al., 1998, Membrane Separation Chemistry in Sugar Processing Applications, Proceedings of the Conference on Sugar Processing Research, Savannah, GA, pp. 248-28.
Vercellotti et al., 1998, SIT Paper 727, Sugar Industry Technologist Annual Meeting, Marseille France, pp. 49-78.
Vercellotti et al., 1996, Proc. Conf. Sugar Processing Res., SPRI, New Orleans, 321-349.

(56) References Cited

OTHER PUBLICATIONS

Wachowicz, 1978, Gazeta Cukrownicza 86:125-127 (Abstract Only: HCAPLUS database record No. 1978:548469).
Wang et al., 2008, Carbohydrate Polymers 74:127-132.
Winter et al., 1992, J. Exp. Mar. Biol. Ecol., 155:263-277.
Wu et al., 2005, Carcinogenesis 26(5):976-980.
Wu et al., 2002, Huanjing Wuran Yu Fangzhi 24(1):13-18 (Abstract Only; HCAPLUS database record No. 2002:439963).
Zhang et al., 2007, Can. J. Physiol. Pharmacol. 85:1116-1123.
Zielinska-Przyjemska et al., 2007 Acta Sci. Pol., Technol. Aliment. 6 (3):75-87.
Zhang et al., 2009, Zhongguo Difangbingxue Zazhi 28(4):381-385 (Abstract Only).
Nagao et al., 2009, Jap. Pharmacol. Therapeut. 37(4):333-344 (Abstract Only).
Ishikura et al., 2008, Jap. Pharmacol. Therapeut. 36(10):931-939 (Abstract Only).
Lee et al., 2008, Hanguk Kikpum Yongyang Kwahak Hoechi 37(5):561-570 (Abstract Only).
Nakamura et al., 2008, Jap. Pharmacol. Therapeut. 36(4):347-357 (Abstract Only).
Hu et al., 2006, Zhongguo Linchuang Kangfu 10(43):79-81 (Abstract Only).
Melby et al., 2007, Daizu Tanpakushitsu Kenkyu 9:138-146 (Abstract Only).
Nakamura et al., 2007, Jap. Pharmacol. Therapeut. 35(6):661-671 (Abstract Only).
Zielinska-Przyjemska et al., 2005, Polski Merkuriusz 19(109):41-47 (Abstract Only).
Kishihara et al., 1986, Kagaku Kogaku Ronbunshu 12(2):199-205 (Abstract Only).
Bray et al., 1999, Endocrine Rev 20(6):805-875.
Goossens et al., 2003, Obesity Rev. 4:43-55.
Kumar et al., 1998, Indian Vet. Med. J. 22:185-188.
Rosenberg et al., 1956, "Response of Growing and Mature Pullets to Continuous Feeding of Cane Final Molasses," Hawaii Agricultural Experiment Station Technical Paper No. 349.
Zheng et al., 2004, In Vivo 18:55-62.
Mehra et al., 1998, Asian-Australasian J. Animal Sci. 11(1):30-34.
Zemel, 2002, J. Am. Coll. Nutr. 21(2):146S-151S.
Han et al., 2003, Phytother. Res. 17:1188-1194.
Kajimoto et al., 2005, J. Health Sci. 51(2)161-171.
Sies et al., 2005, J. Nutrition 135(5):969-972.
"Gekkan Food Chemical," 2001, pp. 72-81, vol. 17, No. 10 (English translation of abstract only).
Han et al., 2003, Phytotherapy Res. 17(10):1188-1194.
Kajimoto et al., 2005, J. Health Sci. 51(2):161-171.
"Shokuhin to Kaihatus," 2000, pp. 15-18, vol. 35 No. 6 (English translation of abstract only).

* cited by examiner

FIGURE 1

| Component | Sugar sample | | | | | | | | | | | | | | | | | | | |
|---|---|---|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 | 17 | 18 | 19 | 20 |
| Moisture (g/100 g) | 0.01 | 0.01 | 0.01 | 0.02 | 0.80 | 0.51 | 1.14 | 1.64 | 0.16 | 1.06 | 1.54 | 0.11 | 0.08 | 0.20 | 0.07 | 0.09 | 0.07 | 0.09 | 0.08 | 0.78 |
| Colour (IC units) | 803 | 1200 | 1040 | 1080 | 6640 | 10790 | 8430 | 6700 | 1990 | 25290 | 17710 | 771 | 848 | 1420 | 776 | 1070 | 763 | 1460 | 819 | 4030 |
| Total phenolics (mg CE/ 100 g) | 15.9 | 20.9 | 17.4 | 17.1 | 76.2 | 98.1 | 89.1 | 81.7 | 27.7 | 180.3 | 153.8 | 15.1 | 16.2 | 29.3 | 13.0 | 19.4 | 16.2 | 28.4 | 17.7 | 76.5 |
| Antioxidant activity (mg GAE/100g) | 2.5 | 6.4 | 5.5 | 5.3 | 22.1 | 26.3 | 24.4 | 24.4 | 8.1 | 42.3 | 39.4 | 4.5 | 5.5 | 8.9 | 4.2 | 6.0 | 4.6 | 10.0 | 5.9 | 25.3 |
| Fructose (g/100 g) | 0.02 | 0.03 | 0.02 | 0.02 | 0.42 | 0.56 | 0.63 | 0.30 | 0.06 | 0.78 | 1.50 | 0.02 | 0.03 | 0.07 | 0.03 | 0.04 | 0.03 | 0.08 | 0.04 | 0.33 |
| Glucose (g/100 g) | 0.03 | 0.04 | 0.03 | 0.02 | 0.41 | 0.44 | 0.82 | 0.34 | 0.05 | 1.30 | 1.86 | 0.02 | 0.01 | 0.05 | 0.02 | 0.04 | 0.03 | 0.10 | 0.04 | 0.54 |
| Sucrose (g/100 g) | 99.2 | 98.6 | 99.1 | 99.4 | 97.1 | 97.0 | 95.6 | 96.7 | 98.3 | 94.9 | 93.4 | 98.7 | 98.4 | 98.9 | 98.8 | 99.0 | 99.3 | 96.4 | 97.4 | 95.3 |
| t-aconitic acid (mg/ 100 g ) | 13.2 | 19.3 | 14.4 | 13.8 | 48.6 | 32.9 | 58.0 | 80.0 | 21.6 | 3.3 | 24.4 | 12.6 | 14.0 | 28.6 | 20.3 | 17.2 | 6.5 | 31.9 | 17.4 | 84.2 |
| Sodium (mg/kg) | 87 | 23 | 24 | 31 | 43 | 68 | 122 | 86 | 54 | 72 | 75 | 44 | 11 | 24 | 25 | 41 | 15 | 26 | 18 | 51 |
| Potassium (mg/kg) | 396 | 204 | 176 | 116 | 782 | 948 | 976 | 1427 | 264 | 636 | 1054 | 372 | 229 | 626 | 121 | 473 | 275 | 331 | 114 | 1189 |
| Calcium (mg/kg) | 356 | 66 | 117 | 46 | 335 | 279 | 410 | 683 | 139 | 242 | 385 | 329 | 42 | 114 | 232 | 52 | 29 | 207 | 5 | 323 |
| Magnesium (mg/kg) | 74 | 43 | 33 | 27 | 162 | 159 | 189 | 220 | 68 | 122 | 194 | 28 | 31 | 91 | 27 | 30 | 23 | 45 | 17 | 134 |
| Iron (mg/kg) | 12 | 7 | 10 | 7 | 26 | 13 | 12 | 19 | 18 | 12 | 12 | 8 | 8 | 11 | 15 | 9 | 13 | 11 | 8 | 23 |
| Phosphate (mg/kg) | 59 | 17 | 14 | 2 | 16 | 21 | 22 | 33 | 8 | 16 | 20 | 1 | 9 | 10 | 13 | 8 | 8 | 20 | 3 | 47 |
| Sulphate (mg/kg) | 349 | 290 | 383 | 401 | 567 | 656 | 532 | 648 | 441 | 448 | 449 | 489 | 471 | 533 | 476 | 499 | 586 | 540 | 525 | 599 |
| Chloride (mg/kg) | 52 | 75 | 81 | 32 | 462 | 500 | 513 | 1081 | 145 | 336 | 621 | 90 | 65 | 242 | 33 | 91 | 51 | 85 | 34 | 419 |

Figure 2

| Sample | Volume (l) | Total phenolics (g CE/l) | Anti-oxidants (g GAE/l) | Fructose (g/l) | Glucose (g/l) | Sucrose (g/l) | Total sugars (g/l) | Total Solids (g/100 g) | Ash (g/100g) | Conductivity (NaCl, M) | A420 | pH | Brix |
|---|---|---|---|---|---|---|---|---|---|---|---|---|---|
| 0.1/0 | 80+ | 8.72 | 3.37 | 25 | 20 | 162 | 207 | 30.8 | 3.8 | 0.22 | 61.2 | 7.57 | 35.0 |
| 0.1/R1 | 34+ | 10.00 | 3.48 | 26 | 20 | 172 | 218 | 32.9 | 4.1 | 0.21 | 81.4 | 7.32 | 39.0 |
| 0.1/P1 |  | 8.56 | 2.95 | 29 | 18 | 169 | 216 | 30.7 | 3.8 | 0.23 | 53.2 | 7.29 | 36.0 |
| 0.1/P2 | 46 | 8.40 | 2.92 | 25 | 18 | 156 | 199 | 30.5 | 3.7 | 0.23 | 53.6 | 7.45 | 35.0 |
| 0.5/0 | 40+ | 5.64 | 1.92 | 22 | 12 | 89 | 123 | 20.1 | 2.5 | 0.20 | 31.3 | 6.77 | 23.0 |
| 0.5/R1 | 25+ | 8.40 | 2.33 | 30 | 18 | 109 | 157 | 23.6 | 2.6 | 0.19 | 39.9 | 6.88 | 27.0 |
| 0.5/RW |  | 6.58 | 2.36 | 8.0 | 4.0 | 126 | 134 | 21.6 | 1.8 | 0.05 | 44.0 | 6.74 | 25.0 |
| 0.5/P1 |  | 0.84 | 0.33 | 13 | 9.6 | 5.8 | 28 | 5.9 | 1.6 | 0.24 | 0.48 | 7.24 | 5.8 |
| 0.5/P2 | 15 | 0.64 | 0.26 | 11 | 7.8 | 2.8 | 22 | 4.8 | 1.5 | 0.24 | 0.33 | 7.15 | 4.8 |
| 0.5/PWC | 80 | 0.42 | 0.16 | 7.1 | 4.5 | 2.8 | 14 | 2.9 | 0.75 | 0.12 | 0.23 | 7.17 | 2.9 |
| RO/0 | 80+ | 0.42 | 0.16 | 7.1 | 4.5 | 2.8 | 14 | 2.9 | 0.75 | 0.12 | 0.23 | 7.17 | 2.9 |
| RO/R1 | 10+ | 0.96 | 0.39 | 15 | 11 | 6.7 | 32 | 6.5 | 1.8 | 0.28 | 0.66 | 7.53 | 6.7 |

Figure 3

| Sample | Volume (l) | Cis-Aconitic (g/l) | Trans-Aconitic (g/l) | Poly-Saccharides (g/l) | Na (mg/l) | K (mg/l) | Ca (mg/l) | Mg (mg/l) | Fe (mg/l) | Cl (mg/l) | $PO_4$ (mg/l) | $SO_4$ (mg/l) |
|---|---|---|---|---|---|---|---|---|---|---|---|---|
| 0.1/0 | 80+ | 2.30 | 8.22 | 11.6 | 1032 | 7376 | 1469 | 661 | 31.4 | 4680 | 147 | 639.3 |
| 0.1/R1 | 34+ | 2.38 | 8.88 | | 1075 | 7878 | 1716 | 732 | 40.2 | 5640 | 223.7 | 663.2 |
| 0.1/P1 | | 2.27 | 7.57 | 5.4 | 1054 | 7622 | 1333 | 640 | 27.2 | 4540 | 98.5 | 640.6 |
| 0.1/P2 | 46 | 2.22 | 7.40 | | 1077 | 7854 | 1355 | 683 | 33.4 | 4680 | 99.2 | 652.2 |
| | | | | | | | | | | | | |
| 0.5/0 | 40+ | 1.45 | 4.87 | | 644 | 4520 | 827 | 425 | 21.7 | 2640 | 62.5 | 411.4 |
| 0.5/R1 | 25+ | 1.81 | 6.10 | 6.5 | 674 | 4706 | 978 | 489 | 26.3 | 2520 | 75.0 | 485.9 |
| 0.5/RW | | 1.81 | 6.34 | | 588 | 4465 | 1680 | 778 | 40.8 | 2652 | 137.5 | 780.0 |
| 0.5/P1 | | 0.025 | 0.081 | | 630 | 4247 | 200 | 120 | 0.2 | 3800 | 2.8 | 52.2 |
| 0.5/P2 | 15 | 0.013 | 0.047 | | 479 | 3178 | 138 | 81 | 0.2 | 3520 | 2.0 | 26.6 |
| 0.5/PWC | 80 | 0.012 | 0.041 | | 267 | 1730 | 66 | 41 | 0.1 | 1560 | 1.1 | 19.3 |
| | | | | | | | | | | | | |
| RO/0 | 80+ | 0.012 | 0.041 | | 267 | 1730 | 66 | 41 | 0.1 | 1560 | 1.1 | 19.3 |
| RO/R1 | 10+ | 0.030 | 0.094 | | 630 | 3800 | 143 | 88 | 0.2 | 3580 | 6.9 | 54.0 |
| | | | | | | | | | | | | |

Figure 4

| Sample | Volume (l) | Total phenolics (g CE/l) | Anti-oxidants (g GAE/l) | Fructose (g/l) | Glucose (g/l) | Sucrose (g/l) | Total sugars (g/l) | Total Solids (g/100g) | Ash (g/100g) | Conductivity (NaCl, M) | A420 | pH | Brix |
|---|---|---|---|---|---|---|---|---|---|---|---|---|---|
| 0.1/0 | 80+ | 6.88 | 2.42 | 25 | 21 | 147 | 193 | 26.5 | 3.1 | 0.21 | 51.4 | 8.07 | 30.0 |
| 0.1/R1 | 30+ | 8.10 | 2.79 | 30 | 20 | 156 | 206 | 28.7 | 3.3 | 0.20 | 64.2 | 7.70 | 32.0 |
| 0.1/P1 |  | 6.84 | 2.31 | 24 | 23 | 151 | 198 | 26.8 | 3.3 | 0.22 | 40.9 | 7.74 | 30.0 |
| 0.1/P2 | 50 | 6.18 | 2.07 | 25 | 17 | 138 | 180 | 25.0 | 3.1 | 0.21 | 35.7 | 7.85 | 28.0 |
| 30/0 | 50+ | 4.60 | 1.46 | 18 | 14 | 68 | 100 | 17.2 | 2.1 | 0.19 | 20.2 | 5.04 | 19.0 |
| 30/R1 | 10+ | 6.30 | 1.91 | 18 | 26 | 61 | 105 | 19.4 | 2.2 | 0.17 | 33.7 | 4.88 | 21.0 |
| 30/P1 |  | 2.76 | 0.88 | 13 | 13 | 74 | 100 | 15.4 | 1.9 | 0.19 | 4.79 | 5.31 | 15.8 |
| 30/P2 | 40 | 2.60 | 0.85 | 15 | 16 | 73 | 104 | 15.1 | 1.9 | 0.19 | 4.47 | 5.34 | 15.4 |
| 0.5/0 | 36+ | 2.60 | 0.85 | 15 | 16 | 73 | 104 | 15.1 | 1.9 | 0.19 | 4.47 | 5.34 | 15.4 |
| 0.5/RW | 16+ | 2.10 | 0.69 | 9.0 | 9.0 | 63 | 81 | 12.0 | 0.9 | 0.07 | 3.80 | 5.39 | 12.3 |
| 0.5/P1 |  | 0.21 | 0.09 | 1.8 | 1.8 | 0.2 | 3.8 | 1.5 | 0.64 | 0.11 | 0.063 | 5.35 | 1.4 |
| 0.5/P2 | 20 | 0.20 | 0.09 | 2.0 | 2.0 | 0.2 | 4.2 | 1.4 | 0.69 | 0.10 | 0.056 | 5.36 | 1.3 |
| 0.5/PW | 70 | 0.11 | 0.04 | 1.0 | 0.8 | BDL | 1.8 | 0.76 | 0.32 | 0.05 | 0.056 | 5.56 | 0.7 |
| 0.5/PWC | 90 | 0.12 | 0.05 | 1.2 | 1.1 | 0.1 | 2.4 | 0.91 | 0.44 | 0.06 | 0.052 | 5.48 | 0.9 |
| RO/0 | 90+ | 0.12 | 0.05 | 1.2 | 1.1 | 0.1 | 2.4 | 0.91 | 0.44 | 0.06 | 0.052 | 5.48 | 0.9 |
| RO/R1 | 20+ | 0.25 | 0.11 | 2.5 | 2.3 | 0.3 | 5.1 | 1.8 | 0.74 | 0.12 | 0.103 | 5.49 | 1.8 |

Figure 5

| Sample | Volume (l) | Cis-Aconitic (g/l) | Trans-Aconitic (g/l) | Poly-Saccharides (g/l) | Na (mg/l) | K (mg/l) | Ca (mg/l) | Mg (mg/l) | Fe (mg/l) | Cl (mg/l) | PO$_4$ (mg/l) | SO$_4$ (mg/l) |
|---|---|---|---|---|---|---|---|---|---|---|---|---|
| 0.1/0 | 80+ | 1.59 | 7.02 | 10.3 | 867 | 5058 | 1021 | 502 | 26.0 | 3540 | 96.1 | 435.0 |
| 0.1/R1 | 30+ | 1.80 | 7.53 | | 897 | 5207 | 1190 | 548 | 35.7 | 4220 | 146.4 | 452.4 |
| 0.1/P1 | | 1.70 | 6.73 | 3.5 | 1018 | 5989 | 1116 | 578 | 21.7 | 3540 | 80.3 | 491.4 |
| 0.1/P2 | 50 | 1.58 | 6.31 | | 945 | 5548 | 1019 | 515 | 18.1 | 3340 | 72.1 | 460.4 |
| 30/0 | 50+ | 1.03 | 4.24 | | 692 | 3971 | 765 | 400 | 15.2 | 2520 | 52.9 | 345.6 |
| 30/R2 | 10+ | 1.16 | 4.82 | | 618 | 3532 | 724 | 375 | 20.9 | 2680 | 61.3 | 324.9 |
| 30/P1 | | 0.93 | 3.76 | 0.20 | 526 | 2988 | 502 | 281 | 3.5 | 1840 | 26.8 | 237.5 |
| 30/P2 | 40 | 0.88 | 3.52 | | 583 | 3288 | 549 | 304 | 3.9 | 180 | 28.6 | 255.3 |
| 0.5/0 | 36+ | 0.88 | 3.52 | | 583 | 3288 | 549 | 304 | 3.9 | 180 | 28.6 | 255.3 |
| 0.5/R1 | 16+ | 0.77 | 3.24 | | 229 | 1290 | 456 | 253 | 3.5 | 180 | 26.3 | 231.4 |
| 0.5/P1 | | 0.024 | 0.027 | | 173 | 932 | 42 | 19 | 0.1 | 900 | 0.7 | 2.6 |
| 0.5/P2 | 20 | 0.021 | 0.024 | | 186 | 977 | 44 | 19 | 0.1 | 900 | 0.9 | 2.3 |
| 0.5/PW | 70 | 0.008 | 0.021 | | 122 | 631 | 27 | 12 | 0.1 | 560 | 1.5 | 2.8 |
| 0.5/PWC | 90 | 0.009 | 0.023 | | 141 | 738 | 32 | 15 | 0.1 | 760 | 1.0 | 1.3 |
| RO/0 | 90+ | 0.009 | 0.023 | | 141 | 738 | 32 | 15 | 0.1 | 760 | 1.0 | 1.3 |
| RO/R1 | 20+ | 0.02 | 0.045 | | 296 | 1592 | 68 | 31 | 0.1 | 1580 | 0.7 | 2.1 |

Figure 13

| Compound | Sample (fraction) / Amount in sample (mg/Kg)[a] | | | | | |
|---|---|---|---|---|---|---|
| | XAD (Acid) | XAD (Basic) | MFP (Acid)[b] | MFP (Basic) | Sugar (Acid)[b] | Sugar (Basic) |
| Caffeic Acid | 168.8 | 207.4 | 12.0 | 9.6 | 0.6 | Not detected |
| Chlorogenic Acid | 368.2 | 123.1 | 26.3 | 2.5 | 0.7 | Not detected |
| p-Coumaric Acid | 1170.9 | 1253.8 | 30.9 | 22.8 | 2.2 | 0.2 |
| Ferulic Acid | 738.8 | 724.1 | 34.7 | 30.8 | 0.5 | Not detected |
| Gallic Acid | Not detected | Not detected | 4.6 | 0.8 | 0.1 | Not detected |
| Syringic Acid | 433.5 | 472.6 | 85.5 | 52.3 | 0.6 | Not detected |
| Vanillic Acid | 2.13 | Not detected | 2.7 | Not detected | Trace[c] | Not detected |
| Apigenin | 34.8 | Not detected | 1.7 | Not detected | 0.12 | Not detected |
| (+)-Catechin | Not detected | 175.2 | 1.0 | 7.0 | 0.22 | Not detected |
| (-)-Catechin Gallate | Not detected | Not detected | 5.9 | Not detected | 0.40 | Not detected |
| Diosmin | 303.6 | 114.3 | 2.3 | 4.1 | Trace | Not detected |
| (-)-Epicatechin | 168.8 | 207.4 | 7.8 | 6.7 | 0.4 | Not detected |
| Kaempferol | Not detected | Not detected | 0.3 | Not detected | Trace | Not detected |
| Luteolin | 18.6 | 41.3 | 0.7 | Not detected | Trace | Not detected |
| Quercetin | 91.3 | 137.1 | 4.7 | 2.6 | Trace | Not detected |
| Rutin | 59.3 | 59.3 | 1.8 | 1.7 | Trace | Not detected |
| Total | 3663.8 | 3515.7 | 222.8 | 140.9 | 6.0 | 0.2 |

Figure 14

|  | MFP-acid | MFP-base | XAD-acid | XAD-base |
|---|---|---|---|---|
|  | Detected in sample | | | |
| Apigenin | Yes | Yes | Yes | Yes |
| (-)-Catechin gallate | Yes | Yes | No | No |
| Chlorogenic Acid | Yes | Yes | Yes | Yes |
| Caffeic acid | Yes | Yes | Yes | Yes |
| Diosmin | Yes | Yes | Yes | Yes |
| Tricin[a] | Not analysed | Not analysed | Yes | Not analysed |
| Luteolin | Yes | Yes | Yes | No |
| Quercetin | Not analysed | Not analysed | Yes | Not analysed |
| Rutin | Yes | Yes | Not analysed | Not analysed |
| Syringic acid | Not analysed | Not analysed | Yes | Not analysed |
| Vanillic acid | Yes | No | Yes | No |

Figure 17

| Component | Process Stream | | | | | | | | | |
|---|---|---|---|---|---|---|---|---|---|---|
| | FEJ | BT | MMF | MM | MME | ESJ | SYR | MOL | RS |
| Total solids (g/100g) (filtered) | 20.0 | 14.1 | 10.7 | - | 0.29 | 13.0 | 7.0 | 7.7 | 35.1 |
| Total solids (g/100g) (unfiltered) | 20.4 | 14.4 | 11.0 | 31.2 | - | 13.0 | 72.3 | 80.0 | 100 |
| Density (g/ml) (filtered) | 1.079 | 1.055 | 1.044 | - | 1.000 | 1.054 | 1.029 | 1.034 | 1.152 |
| Fructose (g/100g DW)$^c$ | 4.5 | 3.2 | 2.0 | - | Nil | 1.6 | 2.2 | 11.7 | BDL |
| Glucose (g/100g DW) | 4.8 | 3.8 | 2.3 | - | Nil | 1.7 | 2.1 | 9.5 | BDL |
| Sucrose (g/100g DW) | 86 | 77 | 76 | - | Nil | 89 | 88 | 42 | 99.3 |
| Polysaccharides (g/100g DW) | - | 0.52 | - | 4.9 | - | - | - | 2.9 | 0.053 |
| Total phenoles (mg catechin equiv/ 100g DW) | 330 | 362 | 402 | - | 1580 | 309 | 391 | 2500 | 21.1 |
| Antioxidant activity (mg gallic acid equiv/100g DW | 68.1 | 75.9 | 142 | - | 563 | 104 | 115 | 726 | 6.7 |
| Fat (g/100g DW) | - | - | - | 3.3 | - | - | - | - | - |
| Total N (g/100g DW) | 0.18 | 0.13 | 0.14 | 0.65 | 0.34 | 0.11 | 0.10 | 0.75 | 0.01 |
| Non-protein N (g/100g DW) | - | - | - | 0.07 | - | - | - | 0.70 | - |
| Protein (g/100g DW) (TN-NPN) x 6.25 | - | - | - | 3.63 | - | - | - | 0.31 | - |

Figure 17 (Cont'd.)

| Component | Process Stream | | | | | | | | |
|---|---|---|---|---|---|---|---|---|---|
| | FEJ | BT | MMF | MM | MME | ESJ | SYR | MOL | RS |
| FALA analysis: | | | | | | | | | |
| Ca (mg/kg)[d] | 45.4 | 148 | 542 | 3547 | - | 238 | 1490 | 8102 | 116 |
| Mg (mg/kg) | 204 | 147 | 185 | 626 | - | 111 | 569 | 3348 | 37.1 |
| Fe (mg/kg) | 127 | 71.2 | 142 | 3958 | - | 2.49 | 32.3 | 172 | 2.82 |
| K (mg/kg) | 1061 | 880 | 1290 | 838 | | 777 | 4122 | 29 320 | 227 |
| UQ analysis: | | | | | | | | | |
| Ca (mg/kg)[d] | | 144 | | 3167 | | | | 8411 | 381 |
| Mg | | 141 | | 721 | | | | 3221 | 32 |
| Na | | 3.3 | | 26 | | | | 428 | 21 |
| K | | 857 | | 1446 | | | | 33679 | 238 |
| Cr | | 0.1 | | 3.6 | | | | 0 | 2.2 |
| Se | | 0.3 | | 2.1 | | | | 3.0 | 6.4 |
| PO4-P | | 114 | | 1484 | | | | 676 | 1.1 |
| SO4-S | | 113 | | 198 | | | | 3330 | 23 |
| Cl | | 723 | | 30 | | | | 22716 | 43 |
| *cis*-aconitic acid (mg/100g DW) | n/a | 47.5 | 58.3 | n/a | 30.7 | 28.6 | 170 | 543 | 4.1 |
| *trans*-aconitic acid (mg/100g DW) | n/a | 489 | 481 | n/a | 640 | 515 | 1723 | 1964 | 60 |

Figure 18

| Component | Process Stream | | | | | | | | |
|---|---|---|---|---|---|---|---|---|---|
| | FEJ | BT | MMF | MM | MME | ESJ | SYR | MOL | RS |
| Total solids (g/100g) (filtered) | - | 13.4 | 13.7 | - | 0.40 | 13.5 | 6.3 | 7.1 | 35.2 |
| Total solids (g/100g) (unfiltered) | - | 13.8 | 13.7 | 23.2 | - | 13.5 | 64.5 | 73.3 | 100 |
| Density (g/ml) (filtered) | - | 1.053 | 1.054 | - | 1.000 | 1.053 | 1.024 | 1.029 | 1.151 |
| Fructose (g/100g DW)[c] | - | 4.0 | 1.4 | - | Nil | 1.5 | 2.0 | 12.8 | BDL |
| Glucose (g/100g DW) | - | 4.1 | 1.3 | - | Nil | 1.6 | 1.7 | 9.2 | BDL |
| Sucrose (g/100g DW) | - | 81 | 91 | - | Nil | 89 | 87 | 52 | 98.8 |
| Polysaccharides (g/100g DW) | - | 0.44 | - | 6.1 | - | - | - | 2.4 | 0.041 |
| Total phenolcs (mg catechin equiv/ 100g DW) | - | 349 | 317 | - | 1593 | 296 | 305 | 2054 | 19.9 |
| Antioxidant activity (mg gallic acid equiv/100g DW | - | 78.0 | 118 | - | 514 | 104 | 105 | 650 | 6.4 |
| Fat (g/100g DW) | - | - | - | 6.2 | - | - | - | - | - |
| Total N (g/100g DW) | - | 0.24 | 0.18 | 1.37 | 0.75 | 0.16 | 0.14 | 0.68 | 0.01 |
| Non-protein N (g/100g DW) | - | - | - | 0.12 | - | - | - | 0.67 | - |
| Protcin (g/100g DW) (TN-NPN) x 6.25 | - | - | - | 7.81 | - | - | - | 0.06 | - |

Figure 18 (Cont'd.)

| Component | Process Stream | | | | | | | | | |
|---|---|---|---|---|---|---|---|---|---|---|
| | FEJ | BT | MMF | MM | MME | ESJ | SYR | MOL | RS | |
| FALA analysis: | | | | | | | | | | |
| Ca (mg/kg)[d] | - | 189 | 332 | 6009 | - | 246 | 2287 | 6300 | 106 | |
| Mg (mg/kg) | - | 141 | 134 | 847 | - | 102 | 918 | 2580 | 32.0 | |
| Fe (mg/kg) | - | 71.3 | 16.1 | 1734 | - | 1.73 | 10.2 | 154 | 3.55 | |
| K (mg/kg) | - | 807 | 989 | 621 | - | 966 | 9558 | 23 870 | 178 | |
| UQ analysis: | | | | | | | | | | |
| Ca (mg/kg)[d] | | 173 | | 5819 | | | | 6652 | 94 | |
| Mg | | 128 | | 820 | | | | 2495 | 31 | |
| Na | | 3.5 | | 3.9 | | | | 265 | 6.7 | |
| K | | 730 | | 965 | | | | 26945 | 255 | |
| Cr | | 0.1 | | 1.5 | | | | 0 | 0.9 | |
| Se | | 0.5 | | 2.8 | | | | 4.1 | 5.3 | |
| PO4-P | | 101 | | 2962 | | | | 556 | 4.7 | |
| SO4-S | | 115 | | 271 | | | | 2168 | 29 | |
| Cl | | 810 | | 52 | | | | 19174 | 28 | |
| *cis*-aconitic acid (mg/100g DW) | n/a | 39.6 | 37.2 | n/a | 50 | 22.2 | 126 | 500 | 3.7 | |
| *trans*-aconitic acid (mg/100g DW) | n/a | 414 | 494 | n/a | 47 | 482 | 1966 | 1688 | 62.1 | |

Figure 19

| Component | Sample Number | | | | | | |
|---|---|---|---|---|---|---|---|
| | 1 | 2 | 3 | 4 | 5 | 6 | 7 |
| Total solids (g/100g) (filtered) | 14.1 | 13.4 | 14.1 | 13.9 | 16.7 | 15.1 | 17.1 |
| Total solids (g/100g) (unfiltered) | 14.4 | 13.8 | 14.6 | 14.3 | 16.8 | 15.4 | 17.2 |
| Density (g/ml) (filtered) | 1.055 | 1.053 | 1.055 | 1.054 | 1.066 | 1.059 | 1.067 |
| Fructose (g/100 g DW) | 4.5 | 4.0 | 3.7 | 3.7 | 2.7 | 2.2 | 2.0 |
| Glucose (g/100 g DW) | 4.8 | 4.1 | 4.2 | 3.9 | 2.2 | 2.3 | 2.2 |
| Sucrose (g/100 g DW) | 86 | 81 | 81.5 | 81.0 | 84.8 | 82.5 | 89.7 |
| Polysaccharides (g/100 g DW) | 0.52 | 0.44 | 0.48 | 0.46 | 0.52 | 0.47 | 0.35 |
| Total phenolics (mg catechin equiv/100 g DW) | 362 | 349 | 427 | 382 | 414 | 384 | 274 |
| Antioxidant activity (mg gallic acid equiv/100 g DW) | 76 | 78 | 110 | 85 | 100 | 101 | 72 |
| Total N (g/100 g DW) | 0.13 | 0.24 | - | - | - | - | - |
| cis-aconitic acid (mg/100 g DW) | 47.5 | 39.6 | 42.8 | 51 | 30.7 | 32 | 36.2 |
| trans-aconitic acid (mg/100 g DW) | 489 | 414 | 294 | 439 | 351 | 374 | 410 |

Figure 20

| Component | Sample Number | | | | | | |
|---|---|---|---|---|---|---|---|
| | 1 | 2 | 3 | 4 | 5 | 6 | 7 |
| Total solids (g/100g) | 31.2 | 23.2 | 27.0 | 25.0 | 24.2 | 25.7 | 26.6 |
| Polysaccharides (g/100 g DW) | 4.9 | 6.1 | 5.9 | 8.2 | 9.5 | 10.8 | 10.6 |
| Total lipid (g/100 g DW) | 3.3 | 6.2 | 4.6 | 5.6 | 7.4 | 6.7 | 7.0 |

Figure 25

| Component | Component fractionation at different pore sizes (%) | | | | | | | | | |
|---|---|---|---|---|---|---|---|---|---|---|
| | 1000 Da | | 5000 Da | | 10 000 Da | | 30 000 Da | | 50 000 Da | |
| | Perm | Ret | Perm | Ret | Perm | Ret | Perm | Ret | Perm | Ret |
| Polyphenols | 63 | 41 | 81 | 24 | 72 | 27 | 72 | 20 | 73 | 23 |
| Antioxidants | 67 | 39 | 76 | 24 | 69 | 30 | 73 | 30 | 72 | 24 |
| Sugars | 89 | 1.1 | 92 | 0.55 | 87 | 0.59 | 93 | - | 100 | - |
| Organic acids | 81 | 1.1 | 89 | 0.5 | 91 | 0.7 | 77 | 0.4 | 93 | 0.6 |
| Total solids | 95 | 7.6 | 98 | 5.0 | 96 | 5.9 | 99 | 6.0 | 99 | 4.9 |

Figure 21

| Component | Sample Number | | | | | | |
|---|---|---|---|---|---|---|---|
| | 1 | 2 | 3 | 4 | 5 | 6 | 7 |
| Total solids (g/100g) (filtered) | 10.7 | 13.7 | 13.6 | 12.4 | 13.9 | 14.5 | 13.0 |
| Total solids (g/100g) (unfiltered) | 11.0 | 13.7 | 13.7 | 12.4 | 13.8 | 14.5 | 13.1 |
| Density (g/ml) (filtered) | 1.044 | 1.054 | 1.054 | 1.049 | 1.054 | 1.057 | 1.051 |
| Fructose (g/100 g DW) | 2.0 | 1.4 | 1.4 | 1.6 | 1.9 | 1.7 | 2.0 |
| Glucose (g/100 g DW) | 2.3 | 1.3 | 1.5 | 1.8 | 1.8 | 1.8 | 2.2 |
| Sucrose (g/100 g DW) | 76.0 | 91.0 | 91.1 | 91.0 | 89.9 | 86.2 | 84.4 |
| Polysaccharides (g/100 g DW) | - | - | - | - | - | - | - |
| Total phenolics (mg catechin equiv/100 g DW) | 402 | 317 | 338 | 327 | 326 | 343 | 329 |
| Antioxidant activity (mg gallic acid equiv/100 g DW) | 142 | 118 | 126 | 131 | 118 | 155 | 135 |
| Total N (g/100 g DW) | 0.14 | 0.18 | 0.16 | 0.16 | 0.14 | 0.14 | 0.13 |
| *cis*-aconitic acid (mg/100 g DW) | 58.3 | 37.2 | 34 | 36.5 | 38.5 | 39.2 | 47.9 |
| *trans*-aconitic acid (mg/100 g DW) | 481 | 494 | 480 | 459 | 466 | 458 | 522 |

Figure 22

| Component | Sample Number | | | | | | |
|---|---|---|---|---|---|---|---|
| | 1 | 2 | 3 | 4 | 5 | 6 | 7 |
| Total solids (g/100g) (filtered) | 0.3 | 0.4 | 0.5 | 0.4 | 0.4 | 0.7 | 0.9 |
| Total solids (g/100g) (unfiltered) | - | - | - | - | - | - | - |
| Density (g/ml) (filtered) | 1.000 | 1.000 | 1.001 | 1.000 | 1.000 | 1.002 | 1.003 |
| Fructose (g/100 g DW) | N/D | N/D | N/D | N/D | N/D | N/D | N/D |
| Glucose (g/100 g DW) | N/D | N/D | N/D | N/D | N/D | N/D | N/D |
| Sucrose (g/100 g DW) | N/D | N/D | N/D | N/D | N/D | N/D | N/D |
| Polysaccharides (g/100 g DW) | - | - | - | - | - | - | - |
| Total phenolics (mg catechin equiv/100 g DW) | 1580 | 1593 | 1423 | 1495 | 1521 | 1266 | 1356 |
| Antioxidant activity (mg gallic acid equiv/100 g DW) | 563 | 514 | 353 | 502 | 616 | 315 | 334 |
| Total N (g/100 g DW) | 0.34 | 0.75 | 0.77 | 0.45 | 1.03 | 0.42 | 0.33 |
| cis-aconitic acid (mg/100 g DW) | 30.7 | 50 | 151 | 51.6 | 177 | 147 | 340 |
| trans-aconitic acid (mg/100 g DW) | 640 | 47 | 765 | 409 | 2450 | 760 | 1730 |

Figure 23

| Component | Sample Number | | | | | | |
|---|---|---|---|---|---|---|---|
| | 1 | 2 | 3 | 4 | 5 | 6 | 7 |
| Total solids (g/100g) (filtered) | 7.7 | 7.1 | 7.5 | 7.9 | 7.8 | 7.8 | 7.7 |
| Total solids (g/100g) (unfiltered) | 80.0 | 73.3 | 77.8 | 81.7 | 80.2 | 80.6 | 80.7 |
| Density (g/ml) (filtered) | 1.034 | 1.029 | 1.031 | 1.033 | 1.032 | 1.032 | 1.032 |
| Fructose (g/100 g DW) | 11.7 | 12.8 | 8.9 | 9.5 | 13.2 | 10.8 | 11.6 |
| Glucose (g/100 g DW) | 9.5 | 9.2 | 7.5 | 7.7 | 9.2 | 9.3 | 10.3 |
| Sucrose (g/100 g DW) | 42.0 | 52.0 | 46.6 | 45.3 | 38.2 | 37.0 | 38.7 |
| Polysaccharides (g/100 g DW) | 2.9 | 2.4 | 2.8 | 3.0 | 2.9 | 3.0 | 3.1 |
| Total phenolics (mg catechin equiv/100 g DW) | 2500 | 2054 | 2351 | 2503 | 2733 | 2713 | 2700 |
| Antioxidant activity (mg gallic acid equiv/100 g DW) | 726 | 650 | 804 | 864 | 869 | 899 | 873 |
| Total N (g/100 g DW) | 0.75 | 0.68 | - | - | - | - | - |
| cis-aconitic acid (mg/100 g DW) | 543 | 500 | 597 | 570 | 597 | 589 | 578 |
| trans-aconitic acid (mg/100 g DW) | 1964 | 1688 | 1920 | 2020 | 1960 | 2210 | 2120 |

Figure 24

| Component | Sample Number | | | | | | |
|---|---|---|---|---|---|---|---|
| | 1 | 2 | 3 | 4 | 5 | 6 | 7 |
| Total solids (g/100g) (filtered) | 35.1 | 35.2 | 35.0 | 35.1 | 34.9 | 35.0 | 35.0 |
| Total solids (g/100g) (unfiltered) | 100 | 100 | 99.9 | 99.9 | 99.5 | 99.6 | 99.5 |
| Density (g/ml) (filtered) | 1.152 | 1.151 | 1.151 | 1.151 | 1.151 | 1.151 | 1.151 |
| Fructose (g/100 g DW) | BDL | BDL | BDL | BDL | BDL | BDL | BDL |
| Glucose (g/100 g DW) | BDL | BDL | BDL | BDL | BDL | BDL | BDL |
| Sucrose (g/100 g DW) | 99.3 | 98.8 | 99.5 | 99.4 | 98.8 | 99.3 | 98.9 |
| Polysaccharides (g/100 g DW) | 0.053 | 0.041 | 0.068 | 0.044 | 0.080 | 0.063 | 0.091 |
| Total phenolics (mg catechin equiv/100 g DW) | 21.1 | 19.9 | 22.6 | 24.8 | 61.1 | 43.0 | 60.0 |
| Antioxidant activity (mg gallic acid equiv/100 g DW) | 6.7 | 6.4 | 8.3 | 8.7 | 21.6 | 15.5 | 21.3 |
| Total N (g/100 g DW) | 0.01 | 0.01 | - | - | - | - | - |
| cis-aconitic acid (mg/100 g) | 4.1 | 3.7 | 4.5 | 4.1 | 8.6 | 7.1 | 8.3 |
| trans-aconitic acid (mg/100 g) | 60 | 62.1 | 74 | 60 | 177 | 111 | 156 |

Figure 26

| Component | Sample Number | | | | | | | | |
|---|---|---|---|---|---|---|---|---|---|
| | 1 | 2 | 3 | 4 | 5 | 6 | 7 | 8 | 9 |
| Total solids (g/100g) | 1.1 | 1.5 | 1.4 | N/T | 0.9 | 0.8 | 0.5 | 0.8 | 1.2 |
| Brix | 1.1 | 1.4 | 1.4 | N/T | 1.0 | 0.8 | 0.5 | 0.8 | 1.2 |
| Density (g/ml) | 1.002 | 1.003 | 1.003 | N/T | 1.002 | 1.001 | 1.000 | 1.001 | 1.003 |
| Colour ($A_{420}$) | 0.5 | 0.8 | 0.5 | N/T | 0.4 | 0.5 | 0.4 | 0.5 | 0.7 |
| Fructose (g/100 g DW) | 0.7 | 1.0 | 1.4 | N/T | BDL | BDL | BDL | 1.1 | 1.3 |
| Glucose (g/100 g DW) | 1.6 | 1.5 | 1.3 | N/T | BDL | BDL | BDL | 1.0 | 1.2 |
| Sucrose (g/100 g DW) | 85.1 | 80.6 | 71.0 | N/T | 88.5 | 69.3 | 75.3 | 71.7 | 74.7 |
| Total phenolics (mg catechin equiv/100 g DW) | 729 | 629 | 752 | N/T | 712 | 855 | 985 | 1093 | 687 |
| Antioxidant activity (mg gallic acid equiv/100 g DW) | 297 | 318 | 327 | N/T | 340 | 427 | 403 | 452 | 304 |

EXTRACTS DERIVED FROM SUGAR CANE AND A PROCESS FOR THEIR MANUFACTURE

This application is a national phase application pursuant to 35 U.S.C. §371 of International Application No. PCT/AU2007/001382, filed Sep. 19, 2007, which claims priority to Australian Application No. 2006905179, filed Sep. 19, 2006.

FIELD OF THE INVENTION

The present invention relates to extracts derived from sugar cane which comprise a mixture of one or more polyphenols, one or more carbohydrates, one or more minerals and one or more organic acids. In addition, the invention relates to a process for refining sugar cane derived extracts as well as other phytochemical extracts.

BACKGROUND OF THE INVENTION

In this specification where a document, act or item of knowledge is referred to or discussed, this reference or discussion is not an admission that the document, act or item of knowledge or any combination thereof was at the priority date, publicly available, known to the public, part of common general knowledge; or known to be relevant to an attempt to solve any problem with which this specification is concerned.

Cane Sugar Refining

After being mechanically harvested, sugar cane is transported to a mill and crushed between serrated rollers. The crushed sugar cane is then pressed to extract the raw sugar juice, while the bagasse (leftover fibrous material) is used for fuel. The raw juice is then heated to its boiling point to extract any impurities, then lime and bleaching agents are added and mill mud is removed. The raw juice is further heated under vacuum to concentrate and increase Brix value. The concentrated syrup is seeded to produce bulk sugar crystals and a thick syrup known as molasses. The two are separated by a centrifuge and the molasses waste stream is collected for use as a low-grade animal feedstock. A flow chart of this process appears below.

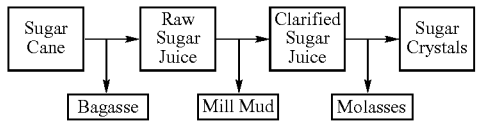

The sugar refining process thus generates a large number of products including raw juice, bagasse, mill mud, clarified juice, etc.

The bulk sugar crystals from the above process are further refined to produce many commercially available sugar products. For example, the further refining may include mixing the bulk sugar crystals with a hot concentrated syrup to soften the outer coating on the crystals. The crystals are then recovered by centrifuge and subsequently dissolved in hot water, a step that is sometimes called affination. This sugar liquor is then further purified by carbonation or phosfloatation, filtration, decolourisation and then seeded with fine sugar crystals. Once the crystals have grown to the requisite size, the crystals are separated from the syrup by centrifuge, then dried, graded and packaged. There may be several repetitions of recovering sugar crystals from the sugar liquor. The dark sugar syrup which is left after all of the sugar crystals have been recovered is also called molasses.

Almost all of the commercially manufactured sugar is white and granulated. White graded sugar is 99.5% sucrose and is made up of crystals averaging 0.6 mm. Caster sugar has an average crystal size of 0.3 mm. Icing sugar is produced by crushing white sugar in a special mill to produce a fine powder.

There are also a range of non-white sugar products including the following:

(a) Coffee sugar is a large grained, brown flavoursome crystal which is produced using the syrups left after extracting the white sugar crystals;

(b) Raw sugar is a straw-coloured granulated sugar produced from sucrose syrups which contain some residual colour and flavour from the sugar cane plant—it is specially selected and handled to ensure a hygienic product;

(c) Golden demerara sugar is a premium raw sugar produced from selected syrups which imparts a rich caramel taste to food; and (d) Brown sugar is a flavoursome, fine-grained and moist crystal produced by further crystallization of the extracted dark coloured sucrose syrups produced in the separation stages of the refining process.

The syrup left after white sugar has been removed is used to make golden syrup and treacle. These syrups are made in a similar fashion with the difference being that golden syrup is decolourised whereas treacle is not.

Cane Sugar Composition

The composition of cane sugar products and waste streams are complex and quite variable—the chemical composition being principally determined by the geographical source of the sugar cane and the method of processing. For example, FIG. 1 sets out the basic compositional elements for raw and brown sugar from the following 20 commercial sources:

1 to 4: Commercial Raw Sugar Brand 1
5 to 8: Commercial Brown Sugar Brand 1
9: Coffee Sugar Crystals Brand 1
10 and 11: Dark Brown Sugar Brand 1
12 to 15: Commercial Raw Sugar Brand 2
17: Commercial Raw Sugar Brand 3
18: Primary Mill Raw Sugar Sample 1
19: Primary Mill Raw Sugar Sample 2
20: Primary Mill Raw Sugar Sample 3

Refining Sugar Products

Molasses and other products of the sugar refining process, especially the thick syrups and juices, are complex mixtures of substances. Typically they are difficult to refine further and there are often substances in the compositions that poison standard separating materials. Molasses and the other thick syrups and juices typically comprise polyphenols, polysaccharides, peptides and proteins, minerals, organic acids, and mono and disaccharides.

Molasses, golden syrup and treacle have been used as a health food since the early 20th century and there have been claims that they are good therapies or cures for a wide range of disorders. However the strong taste make them unpalatable to many people and the high viscosity of treacle and molasses makes them difficult to handle and to incorporate into other foodstuffs. Dark sugars such as brown and light brown sugars can be produced by spraying back molasses onto white refined sugar. Due to the content of reducing sugars, colorants and moisture these finished products clump on storage are hygroscopic which limits commercial and industrial use, and discolour many foods. A sugar with high amounts of molasses and sugar milling waste stream products to promote health with reduced hygroscopic properties, improved flow and lighter colour would be desirable.

The other products of cane sugar refining such as bagasse and mill mud are known to include potentially useful substances but their hitherto intractable nature has meant that they are usually thrown away as waste. It would be desirable to have a method to incorporate these valuable waste stream extracts into finished products including, but not limited to sugar.

The inventors' earlier international patent application no WO 2005/117608 teaches one method of extracting useful extracts from the in-process and waste stream products of sugar manufacturing. The methods disclosed in that application produce an extract which is high in polyphenols and which is useful for use in methods such as that disclosed in international patent application no PCT/AU2006/000769. However, this extract does not always reflect the complexity of the contents of the raw material.

List of Abbreviations
BDL Below Detectable Limit
CE Catechin Equivalents
DW Dry Weight
GAE Gallic Acid Equivalents
GI Glycaemic Index
IC or ICUMSA International Commission for Uniform Methods of Sugar Analysis
MF Microfiltration
N/D Not Detected
N/T Not Tested
XAD Ion exchange separation. Whilst the specification refers to the use of the XAD brand of resins, the invention is not limited to this brand of resin and it is possible to use any brand of resin which can be used in ion exchange separations.

SUMMARY OF THE INVENTION

The present invention provides extracts derived from sugar cane and a process for their production.

According to a first aspect of the invention, there is provided an extract derived from sugar cane having GI or burn rate reducing characteristics wherein the extract comprises a mixture of one or more polyphenols, one or more carbohydrates, one or more minerals and one or more organic acids.

The actual level of polyphenols in the extract of sugar cane will depend on the precise method used for its manufacture and the batch of sugar cane used as raw material. For example, an extract produced using XAD after the fractionation by molecular weight would contain between 15 to 30% polyphenols by weight. In contrast, an extract produced using ultrafiltration and microfiltration (without any XAD) would contain between 1 to 3% by weight of polyphenols.

In one preferred embodiment, the polyphenols in the extract of cane sugar are selected from the group consisting of p-coumaric acid, ferulic acid, syringic acid, caffeic acid, chlorogenic acid, (−)epicatechin, apigenin, (+)catechin, quercetin, diosmin, rutin and mixtures thereof.

The extract of sugar cane comprises some carbohydrates which improves its taste whilst still maintaining its GI lowering characteristics. Typically, the extract comprises carbohydrates such as monosaccharides, disaccharides, oligosaccharides and both soluble and insoluble polysaccharides. The extract may also contain xylan derived mono, di, tri and oligosaccharides, such as xylobiose, xylotriose and xylose. The extract may include carbohydrates having GI increasing characteristics such as sucrose and glucose. However, the amount of GI increasing carbohydrates in the extract is not sufficient to detract significantly from the GI reducing characteristics of the extract as a whole. Further, the extract can comprise some carbohydrates and maintain its usefulness for applications such as body composition redistribution as disclosed in international patent application no PCT/AU2006/000769.

The extract of sugar cane comprises minerals including mineral complexes. Typically, the minerals are selected from magnesium, potassium, magnesium, calcium and mixtures thereof. Other minerals which may be present include anions such as phosphate, sulphate and chloride.

The extract of sugar cane comprises organic acids. Typically, the organic acids are selected from the group consisting of c-aconitic acid, citric acid, phosphoric acid, gluconic acid, malic acid, t-aconitic acid, succinic acid, lactic acid and mixtures thereof.

In one preferred embodiment, there is provided an extract derived from sugar cane having GI or burn rate reducing characteristics wherein the extract is a powder which comprises 1.5 to 2.5 wt % of one or more polyphenols, 50 to 80 wt % of one or more carbohydrates, 1 to 3 wt % of one or more minerals and 1 to 3 wt % of one or more organic acids.

In another preferred embodiment, there is provided an extract derived from sugar cane having GI or burn rate reducing characteristics wherein the extract is a syrup which comprises 3.5 to 6 g CE/l of one or more polyphenols, 80 to 220 g/l of one or more carbohydrates, 3 to 5.5 g/l of one or more minerals and 3 to 6 g t-aconitic/l of one or more organic acids.

Typically the extract of the present invention further comprises additional components such as policosanols, phytosterols, lipids, phospholipids, protein, antioxidants, phytosterols such as 1-octacosanol, campesterol, stigmasterol, β-sitosterol, oligosaccharides such as raffinose, 1-kestose, theanderose, 6-kestose, panose, neo-kestose and nystose, aliphatic alcohols, vitamins, gums and neutral and polar lipids, flavonoids (8 subgroups: Flavonols (eg quercetin, kaempferol,myricetin andisorhamnetin); Flavones (eg luteolin, tricin and apigenin); Flavanones (eg hesperetin, naringenin anderiodictyol); Flavan-3-ols (eg catechin, gallocatechin, epicatechin, epigallocatechin, epicatechin 3-gallate, epigallocatechin 3-gallate and theaflavin); Anthocyanidins (eg cyanidin, delphinidin, malvidin, pelargonidin, peonidin and petunidin); Anthocyanosides; Curcuminoids; and Proanthocyanins) and their derivatives, including but not limited to, natural and synthetic conjugates such as glycosides, glucosides, galactosides, galacturonides, ethers, esters, arabinosides, sulphates, phosphates; aldopentoses (xylose, arabinose) aldohexoses (mannose), ketopentoses, ketohexoses (fructose), kestoses, soluble gums, aliphatic alcohols (and complexes), waxes (and complexes), polysaccharides and fibre (soluble and insoluble), oligosaccharides, non-nitrogenous compounds, mineral complexes (organic iron and other minerals), phytochemical complexes (including but not limited to glucosides, glycosides, glycosylates, esters, glucopyranosides etc), chlorophyll, phytosterols (and complexes), phytostanols (and complexes), hydrolysed celluloses and phospholipids. The term "policosanols", within the scope of the present invention, refers to the family of aliphatic alcohols and their derivatives, complexes or analogues which are found naturally in sugar cane. Examples include long chain fatty alcohols such as octacosanol, triacontanol, dotriacontanol, tetracosanol, hexacosanol, tetratriacontanol, hexatriacontanol and docosanol.

In one preferred embodiment, the extract is a syrup derived from molasses and the extract has the following composition:

| Component | Range | Preferred |
|---|---|---|
| Polyphenols (g CE/l) | 3.5-6.0 | 4-5 |
| Antioxidant (g GAE/l) | 1.2-2.4 | 1.5-1.8 |
| Organic Acids (g/l) (t-aconitic acid) | 3-6 | 4-5 |
| Total Minerals (g/l) | 3-5.5 | 4-5 |
| Carbohydrates (g/l) | 80-220 | 120-170 |
| Color (absorbance at 420 nm) | 5-10 | 6-8 |
| Brix (degrees) | 15-27 | 20-24 |

The above table refers to a preferred extract as it exits the manufacturing equipment. This extract may be modified prior to its inclusion in commercial products. For example, the levels will change as the extract is concentrated to form a syrup with a higher Brix or a powder. All such concentrated extracts are included within the scope of this invention.

The extract can be derived from any product derived from sugar cane including the sugar cane milling process, the sugar cane refining process to make sugar, and other processes using sugar cane products such as the manufacture of ethanol from molasses as part of the manufacture of rum. The extract can be derived from the raw materials, in-process products, by-products, final products and waste streams. For example, the sugar cane derived product may be the feed stream of raw sugar cane juice, clarified juice and concentrated juice syrup, treacle, molasses (obtained from a primary mill or refinery), golden syrup, brown sugar, bagasse, biodunder, field trash, growing tips, pulp, cane strippings, pith and mill mud. Preferably, the extract is derived from molasses.

In another embodiment, the extract may be a combination of extracts from different sugar cane products. For example, the desired phytochemical profile may be obtained by combining an extract of molasses with an extract of biodunder. All such combined extracts are within the scope of this invention.

The physical characteristics of the extracts of the present invention will depend on their overall chemical composition. Depending on the processing methods applied, the extracts may be concentrated by evaporation generating a syrup, or alternatively, the extract could be fully dried to produce a powder. This ability to prepare extracts having different physical properties increases the commercial utility of the extracts. Depending on their physical characteristics and chemical composition the extracts will be suitable for various uses.

METHOD OF PREPARING THE EXTRACTS OF THE PRESENT INVENTION

In a preferred embodiment, the extract is produced using a method which comprises as one of its steps a fractionation by molecular weight and size.

The fractionation by molecular weight maintains in the final extract the natural mixture of phytochemicals that exists in the sugar cane itself. Prior methods used separation processes which removed most of the carbohydrates, minerals and organic acids and the resultant extract was not representative of the natural balance that existed in the sugarcane.

The extracts of the present invention are derived from sugar cane product, preferably molasses from the cane sugar refining processes. The extract may be obtained from the sugar cane product by various methods, or combinations of methods, such as:

solvent and counter-current extraction using non-aqueous or aqueous solvents;

separation of components falling within a specific molecular weight range by size exclusion processing methods such as gel permeation chromatography or ultrafiltration; and separation of the low and high molecular weight components using chromatographic techniques or combinations of techniques such as ion exchange chromatography, hydrophobic chromatography and ion exchange chromatography using fractional elution by stepwise increase in pH or with solvents such as ethanol.

The extracts may be further processed by standard techniques such as microfiltration, reverse osmosis, gel permeation, vacuum evaporation and freeze drying, spray drying and tunnel drying.

Filtration Method

In a preferred embodiment of the present invention, the extract is prepared by a method comprising the steps of:
(a) heating a solution of the cane sugar derived product,
(b) adjusting the solution pH to >7,
(c) precipitating salts from the solution or matrix,
(d) separating the precipitate from the solution or matrix, and
(e) fractioning the solution or matrix by ultrafiltration or similar process to isolate desired extracts.

Gel Permeation Method

In a preferred embodiment of the present invention, the extract is prepared by a gel permeation method comprising the steps of:
(a) heating a solution of the cane sugar derived product,
(b) adjusting the solution pH to >7,
(c) precipitating salts from the solution or matrix,
(d) separating the precipitate from the solution or matrix, and
(e) passing the solution or matrix down a chromatographic column and collecting eluted fractions.

The preferred conditions for steps (a) to (d) are essentially the same as described in respect of the filtration method. Typically step (e) would be carried out at a temperature of 15 to 25° C., preferably 20 to 25° C.

Uses of the Extract

The extracts of the present invention represent new products which are economically useful and can be used in a wide variety of applications. The extracts as described herein may be used in a therapeutic capacity in order to treat and/or prevent the many conditions which are considered to be responsive to antioxidants, including but not limited to, cardiovascular disease, atherosclerosis, hypertension, thrombosis, Type II diabetes, obesity, dementia, cancer, HIV aids, degenerative conditions associated with aging, diseases caused by oxidative damage, and changing body composition as described in international patent application no PCT/AU2006/000769. It is expected that these natural extracts will be better absorbed and may show improved efficacy compared to conventional sources of the components. In populations, which are considered "high-risk" for CVD or any of the oxidation related disorders, it is contemplated that the compositions and foodstuffs to which the extracts are added could be used in primary, secondary and tertiary treatment programs.

The doses of the extracts will vary depending upon, among other factors, the mode of delivery (ie how and into which food, beverage, nutraceutical, cosmaceutical or pharmaceutical the derivatives are ultimately incorporated), the patient size and condition, the result to be achieved, as well as other factors known to those skilled in the art of food additives and medicinal agents. It will also be recognized that the provision of much larger daily doses of the derivatives are not harmful to the animal host, as excess will simply pass through normal excretory channels.

The dose may depend, for example, on the desired reduction in GI. For example, to reduce GI in sugar, the total polyphenol content needs to range from 25-30 mg/100 g sugar. The extract according to the invention can be used to prepare the low GI products described in international patent application no WO 2005/117608, including those where the extract is used in conjunction with other GI lowering compounds such as galactose, arabinose, kestose, oligofructose, or cellulose.

The extracts of the present invention may be incorporated directly and without further modification into a food, nutraceutical, cosmaceutical or beverage by techniques such as mixing, infusion, injection, blending, dispersing, emulsifying, conching, extrusion, immersion, spraying, coating and kneading. The extract can be used to impregnate commonly used food ingredients such as fibre (chicory, sugar cane bagasse and other food grade fibres) and flours prepared from a range of cereal sources. Alternatively, these extracts may be applied directly onto a food or into a beverage by the consumer prior to ingestion. These are simple and economical modes of delivery.

The extracts of the present invention may also be incorporated into food products using the delivery systems described in international patent application no PCT/AU2006/000761.

Pharmaceutical and Cosmaceutical Dosage Forms:

It is contemplated within the scope of the present invention that the extracts of the present invention may be incorporated into various conventional pharmaceutical and cosmaceutical preparations and dosage forms such as tablets (plain and coated) for use orally, bucally or sublingually, capsules (hard and soft, gelatin, with or without additional coatings), powders, granules (including effervescent granules), pellets, microparticulates, solutions (such as micellar, syrups, elixirs and drops), lozenges, pastilles, ampoules, emulsions, microemulsions, ointments, creams, suppositories, gels, and transdermal patches, other transdermal delivery methods involving active and passive transport, depot preparations, enteral solutions, parenteral preparations, intravenous solutions, modified release dosage forms together with customary excipients and/or diluents and stabilizers.

The extracts may also be impregnated, mixed, emulsified, sprayed or coated onto carriers such as cellulose, methycellulose, dextrose, cyclodextrose, cyclodextrin, maltitol, fibre and fibre containing bioactives to improve delivery. Delivery may also be enhanced with a range of surfactants, lipids, complexes, solvents and co-solvent pharmaceutical delivery systems known in the pharmaceutical art to improve bioavailability, absorption and efficacy.

Foods/Beverages/Nutriceuticals:

As used herein, the term "food" or "food product" includes any edible product, such as but not limited to confectioneries, supplements, snacks (sweet and savoury), cocoa-containing foods, flavours, beverages, dietary supplements and formulations including supplements used in animal health and nutrition. Additional ingredients desired in the resulting food product may be added at any point in the process. In one embodiment of the invention, the extracts are in the form of syrups that can be used as substitutes for regular glucose and high fructose corn syrups from wheat, corn, agave, stevia etc., as a lower Glycemic Index (GI) option.

The extracts of the present invention may be incorporated into foods, beverages and nutriceuticals, including, without limitation, the following:

Dairy Products—such as cheeses, butter, milk and other dairy beverages, spreads and dairy mixes, ice cream and yoghurt;

Fat-Based Products—such as margarines, spreads, mayonnaise, shortenings, cooking and frying oils and dressings;

Cereal-Based Products—comprising grains (for example, bread and pastas) whether these goods are cooked, baked or otherwise processed;

Confectioneries—such as chocolate, candies, chewing gum, desserts, non-dairy toppings, sorbets, icings and other fillings;

Sports nutrition products including powders, pre-mixes, juices, energy bars, isotonic drinks and gelatine, starch based or pectin jellies;

Beverages—whether hot or cold (coffee, tea, cocoa, cereal, chicory and other plant extract based beverages), alcoholic or non-alcoholic and including colas and other soft drinks, juice drinks, dietary supplement, instant pre-mixes and meal replacement drinks.

Miscellaneous Products—including eggs and egg products, processed foods such as soups, pre-prepared pastas.

Similarly, food grade ingredients such as soluble fiber (e.g. oligofructosaccharide), insoluble fiber (e.g. sugar cane fiber, oatbran), flour, starch, modified starch, gelatine, or other food, pharmaceutical or cosmetic ingredients impregnated with or containing the extract according to the invention, can produce a unique food ingredient with enhanced levels of polyphenols, policosanols, phytosterols and other phytochemicals derived from sugarcane. Delivery may also be enhanced with a range of surfactants, lipids, emulsifiers, complexes, solvents and co-solvent food and cosmetic delivery systems known in the art to improve dispersion, absorption and efficacy.

The extract according to the invention is particularly useful for increasing the active phytochemical content of coffee products without increasing bitterness. Roasting coffee beans causes the development of the myriad desired flavours of coffee. The roasting also causes the bitter taste of coffee which is related to an increase in the level of the antioxidants chlorogenic acid lactones and phenylindanes. The more that coffee beans are roasted, the more chlorogenic lactones and phenylindanes are produced. The extract of the invention can be used to increase the level of active phytochemicals (such as polyphenols) in coffee products making the coffee products useful for applications such as those disclosed in international patent application no PCT/AU2006/00076.

The present invention includes food products comprising an extract according to the invention alone as the active ingredient or in combination with other active ingredients.

Low GI Products

In a particularly preferred application the extracts of the present invention may be utilized in a formulation strategy directed to the reduction of GI. The extract of the invention can be used to prepare low GI products, such as those disclosed in international patent application no WO2005/117608, but which have a higher antioxidant content and a better taste than the extracts exemplified in that specification. The extracts according to the present invention in the form of a liquid extract can be sprayed onto standard sugar (whether derived from sugar cane or sugar beets) to produce a low GI sugar. The extracts according to the present invention in the form of a liquid extract can also be sprayed onto other carriers such as flour, starch or fibre thus increasing the levels of bioactives in these food ingredients. The extract used for this application preferably has sufficient sucrose content to assist the extract to adhere to the standard sugar crystals and to minimise impairing the taste of the sugar.

For a low GI product, it is preferable to have low glucose levels. The glucose content of the molasses or other products generated in the sugar processing stream can be reduced using enzymes such as glucose oxidase (GO) which digest glucose. It will be known by those skilled in the art that a combination of glucose oxidase and catalase are typically used to ensure that any hydrogen peroxide is removed, and that the oxygen generated is used by the GO to reduce glucose levels. The method of the invention may also incorporate any other method to reduce glucose in the molasses and other products generated in the processing stream which is then reincorporated in the manufacturing process to reduce the GI of the sugar product or used alone as a food, dietary supplement or pharmaceutical. This may include, but is not limited to, fermentation, or encouragement of glucose digestion through other chemical, and/or thermal reactions prior to, during or after the ultrafiltration and ion exchange processes. Affination syrup and other sugar refinery process or waste streams containing low amounts of reducing sugars are particularly useful sources as feedstocks to produce low GI products. By-products of fermentation and distillation are also useful feedstocks.

The method of the invention may also be used to prepare product for use in the methods and products disclosed in international patent application no WO 2005/117608 or international patent application no PCT/AU2006/00076.

Refining Process

According to a second aspect of the invention, there is provided a process for producing an extract of sugar cane comprising the steps of:
(a) heating and diluting a sugar cane derived product until the viscosity of the resulting solution or matrix is less than or equal to about 100 centipoise at a temperature in the range of from 40 to 60° C.;
(b)(i) centrifuging the product of step (a); or alternatively,
(b)(ii) adjusting the pH of the product of step (a) with a base;
(c) heating the product of step (b) to a temperature in the range of from 70 to 80° C. and then maintaining it in that temperature range for a period of time until a precipitate of insoluble calcium and magnesium salts forms;
(d) removing the precipitate and large particulate matter from the product of step (c);
(e) treating the product of step (d) with a fractionation by molecular weight and size to isolate desired extracts.

Preferably, the temperature used in step (a) is about 50° C. Preferably, the viscosity achieved is in the range from 50 to 100 centipoise. Typically, water is used for the dilution in step (a). When the sugar cane derived product is molasses, a ratio of 1:0.8 to 1.2 molasses to water is typically used to provide the desired ratio. The preferred viscosity can also be adjusted by measuring the Brix, in which preferably the range is from 30 to 50 Brix, and more preferably from 35 to 45 Brix.

Preferably, when the pH is adjusted as in step (b)(i), the final pH is in the range of from 7.2 to 9.5. The pH adjustment can be made using any suitable base, such as sodium hydroxide, sodium carbonate ($Na_2CO_3$), potassium carbonate ($K_2CO_3$), bubbling with gaseous carbon dioxide ($CO_2$), or a combination of all the above. Preferably, the pH adjustment occurs using a sodium hydroxide solution.

Preferably, when the diluent is centrifuged, this is carried out using a continuous desludging centrifuge with the supernatant being directly processed through a ceramic or stainless steel membrane (typical 0.10 micron to 1.5 micron, preferably 0.1 to 0.5 micron) using a pressure of about 4 Bar, a flow rate of approximately 30 to 100 1/hour and at a temperature of 30 to 60° C., preferably 35 to 50° C.

Preferably, the temperature in step (c) is about 75° C. Preferably, the period of time is in the range of from 10 to 30 minutes, more preferably about 20 minutes.

Where necessary for the equipment used in step (d), the mixture from step (c) is cooled prior to step (d).

Step (d) can be achieved using any method known to a person skilled in the art for removing a precipitate. Typically it is carried out using a desludging centrifuge or other filtration methods including diatomaceous earth or fine muslin or similar material. For example, the mixture may be passed through a ceramic or stainless steel membrane (0.10 micron to 1.5 micron, preferably 0.1 to 0.5 micron) using a pressure of 4 Bar, a flow rate of 30 to 100 1/hour and at a temperature of 30 to 60° C., preferably 35 to 50° C. The retentate (typically the precipitate from step (d) and large particulate matter) is discarded (typically after washing with water having a pH in the range of from 7.2 to 7.5) and the permeate collected. In some applications, the retentate is not washed but is completely discarded. Alternatively, high speed continuous centrifugation could be used to remove the precipitate and large particulate matter.

In one preferred embodiment, step (e) is undertaken using one or more fractionation filters or membranes selected from the group consisting of ultrafiltration, nanofiltration and mixtures thereof, to isolate desired extracts. The fractionation filters or membranes are known to persons skilled in the art of food processing. For example, the product from step (d) can be treated by passing it though a combination of spirally wound ultrafiltration (UF) membranes with a size exclusion in the range of from 100 kDa to 1 kDa. Preferably from 30 kDa to 50 kDa and/or 1 kDa. Further fractionation can then be achieved with a 0.5 kDa nanofiltration membrane. A person skilled in the art will know that the choice of membrane used will depend on the desired final product, flow rate, pH, pressure, temperature and efficiency across a range of conditions. Typically, step (e) will include diafiltration and both the retentate and permeate will be collected. Typically, step (e) will occur at a temperature in the range of from 30 to 60° C., more typically 35 to 50° C.

In another embodiment of the invention, step (e) is undertaken using gel permeation.

In one embodiment of the invention, step (e) is followed by further refining steps which may include ion exchange, hydrophobic chromatography with further ultrafiltration or nanofiltration, gel permeation or reverse osmosis.

The sugar cane derived product used as starting material for this process can be any product derived from sugar cane including products from the sugar cane milling process, the sugar cane refining process to make sugar, and other processes using sugar cane products such as the manufacture of ethanol from molasses as part of the manufacture of rum. The sugar cane derived product can be the raw materials, in-process products, by-products, final products and waste streams. For example, the sugar cane derived product includes the feed stream of raw sugar cane juice, clarified syrup and concentrated syrup, treacle, molasses (primary mill and refinery), golden syrup, brown sugar, bagasse, biodunder, field trash, cane strippings, pith, growing tips, pulp and mill mud. Preferably, the sugar cane derived product is molasses.

The use of affination syrup, molasses or other process and refining waste products as the starting material, provides a retentate after the use of a 30 kDa membrane that contains large polyphenols, polysaccharides, peptides and proteins, and the permeate will contain smaller polyphenols, minerals, organic acids, and mono, di and polysaccharides. The process of the invention enables the production of a molasses extract containing up to about 90% of the antioxidants contained from the original molasses. The permeate may then be further treated using ion exchange or hydrophobic resin or further ultrafiltration to produce an extract containing the desired profile of polyphenols, minerals, organic acids and carbohydrates. By using the process of the invention, it is possible to minimise any detrimental effects the resin as the substances which would poison the resin have been substantially reduced.

The fractionation filters or membranes are able to separate the material collected in step (e) into a range of functional sugar syrups containing a range of polyphenols as previously specified and different ratios of sucrose, glucose and fructose in combination with a mixture of minerals (eg magnesium and potassium) in ratios similar to that in natural sugar cane juice depending upon the initial feedstock.

The syrups collected using the method of the invention can be used as functional sweeteners in beverages, ice creams and iced confections and in confectionery products including but not limited to fondants, fondant cream centres for chocolate products, truffles, caramels, fudges, gelatin, starch and pectin based gums and jellies and high boiled sweets and toffees. These syrups can also be used in any food application where wheat or corn based glucose syrups or high maltose glucose syrups are used. The fractionation process can be manipulated so that the ratio of monosaccharides to sucrose is sufficient to inhibit sucrose crystallisation in such applications. The syrups while functioning as both sweeteners and crystallisation inhibitors may also deliver additional natural mineral and antioxidant properties to the products.

In one embodiment of the invention, once the fractions are recovered from the method of the invention, they can be further concentrated by a combination of nanofiltration which preferentially removes monovalent anions, reverse osmosis and/or traditional high vacuum evaporation processes. Final solids content of the syrups can range from 65% to 80% w/v with water activities in the range of from 0.2 to 0.3. This further concentration can result in syrups having a shelf life of up to 6 months when stored under suitable conditions such as between 5 and 25° C.

The method of the invention may also be used to prepare product for use in the methods and products disclosed in international patent application no WO 2005/117608 or international patent application no PCT/AU2006/00076. International patent application no WO 2005/117608 discloses a method for preparing a low GI product using ultrafiltration with a 300 kDa membrane and solvent extraction, however this process only extracts about 50% of the antioxidants present in the sugar cane product. The method according to the second aspect of the present invention recovers a higher percentage of the antioxidants present in the sugar cane product.

The method according to the invention may be used to refine phytochemical extracts obtained from other sources.

According to a third aspect of the invention, there is provided a method for refining a phytochemical extract comprising the steps of:
(a) heating and diluting a phytochemical containing extract until the viscosity of the resulting solution or matrix is less than or equal to about 100 centipoise at a temperature in the range of from 40 to 60° C.;
(b)(i) centrifuging the product of step (a); or alternatively,
(b)(ii) adjusting the pH of the product of step (a) with a base;
(c) heating the product of step (b) to a temperature in the range of from 70 to 80° C. and then maintaining it in that temperature range for a period of time until a precipitate of insoluble calcium and magnesium salts forms;
(d) removing the precipitate and large particulate matter from the product of step (c);
(e) treating the product of step (d) with a fractionation by molecular weight and size to isolate desired extracts.

The phytochemical extract may be sourced from a variety of plant sources from which it is known that phytochemicals such as polyphenols may be extracted. Typical sources include, but are not limited to, cocoa beans, tea waste, pod husks, coffee beans, coffee waste, grape pomice, cereals (eg barley, buckwheat, corn, millets, oats, rice, rye, sorghum, wheat), legumes (eg beans and pulses), nuts (eg almonds, betel nuts, cashew nuts, hazelnuts, peanuts, pecans, walnuts), oilseeds (eg rapeseed, canola, soybeans, borage, cottonseed, evening primrose, flaxseed, sesame seeds, sunflowers, olive oil, palm oil, rice bran oil), fruits (eg berries, drupes, pomes, tropical fruits), vegetables (eg carrots, onions, parsnips, potatoes, beetroot, sweet potato, asparagus, celery, endive, lettuce, spinach, avocado, tomato, pepper), beverages (eg tea, coffee, cocoa, beer, wine, cider) and herbal products (eg Echinacea, ginseng, ginkgo biloba, St John's Wort, valerian, kava kava, saw palmetto, black cohosh, Devil's Claw, goldenseal, hawthorn, ginger, liquorice, milk thistle).

These bioactive rich extracts can be used to enhance the level of bioactives in a range of food products such as fruit juices, and dried and processed fruits. One example of a delivery system which can be used with these extracts is disclosed in international patent application no PCT/AU2006/000761.

BRIEF DESCRIPTION OF THE FIGURES

FIG. 1 shows the composition of 20 commercial raw and brown sugars.

FIG. 2 shows the analysis of the extract obtained after membrane filtration of molasses, Group 1 from Example 4.

FIG. 3 shows the analysis of the extract obtained after membrane filtration of molasses, 30 Group 1 from Example 4.

FIG. 4 shows the analysis of the extract obtained after membrane filtration of molasses, Group 2 from Example 4.

FIG. 5 shows the analysis of the extract obtained after membrane filtration of molasses, Group 2 from Example 4.

FIG. 13 shows the concentrations of selected compounds in the three samples investigated as determined by RP-HPLC with UV detection. Results were obtained by expressing against a p-coumaric acid external calibration curve. Individual response factors were not calculated from Example 7.

FIG. 14 is a summary of the information produced by the LC-MS experiments for selected compounds from Example 7.

FIG. 17 shows the composition of sugar processing streams Batch 1 from Example 9.

FIG. 18 shows the composition of sugar processing streams Batch 2 from Example 9.

FIG. 19 shows the composition of buffer tank streams in different batches from Example 9.

FIG. 20 shows the composition of mill mud streams in different batches from Example 9.

FIG. 21 shows the composition of mill mud filtrates in different batches from Example 9.

FIG. 22 shows the composition of mill mud extracts in different batches from Example 9.

FIG. 23 shows the composition of molasses streams in different batches from Example 9.

FIG. 24 shows the composition of raw sugars in different batches from Example 9.

FIG. 25 shows the composition of fractions of molasses by membrane ultrafiltration from Example 9.

FIG. 26 shows the composition of mill mud extracts in different batches from Example 13.

EXAMPLES

Figure 6:
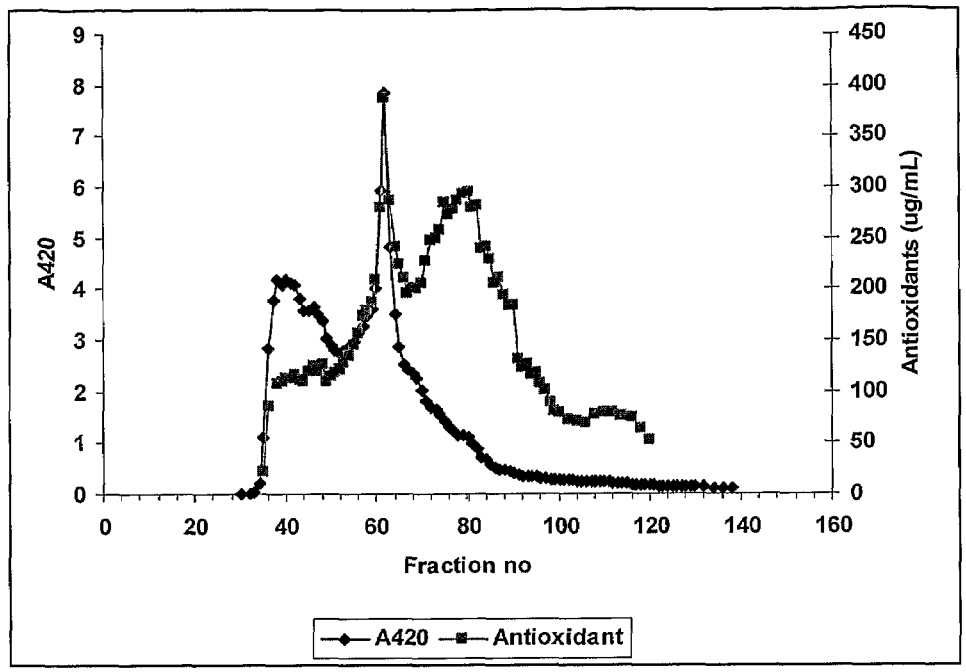
FIG. 6 shows the gel filtration of molasses on Bio-Gel P-2 showing A420 and antioxidant activity for Run 3 from Example 6.

Various embodiments/aspects of the invention will now be described with reference to the following non-limiting examples.

Example 1

In this example, molasses was treated using the method according to the second aspect of the invention.

Method

Step 1: Molasses was diluted with water in a 1:1 ratio and adjusted to a pH of 7.2 with 5% NaOH solution, and heated to 75° C. The mixture was allowed to stand for 30 minutes at 75° C. until a precipitate of Ca and Mg salts formed.

Step 2: The mixture from step (1) was passed through ceramic or stainless steel membrane with a pore size between 0.1 to 0.5 micron at a temperature between 35 to 50° C. and the retentate of insoluble Ca and Mg salts and large particulate matter from the molasses was discarded.

Step 3: The permeate from step (2) was passed through a 30 kDa ultrafiltration membrane at a temperature between 35 to 50° C., and the retentate was diafiltered, and both the retentate (R1) and the permeate (P1) were collected. The retentate (R1) contained large polyphenols, polysaccharides, peptides and proteins etc and the permeate (P1) contained smaller polyphenols, minerals, organic acids, and mono and disaccharides. The retentate (R1) was placed to one side for further work later.

Step 4: The permeate P1 was passed through a hydrophobic resin and all unbound material was washed off with water. The eluant (E1) was collected and found to contain sugars, organic acids, polyphenols and minerals.

Step 5: The bound material (hydrophobic) was desorbed with ethanol (70% v/v). The recovered desorbed eluant (E2) was found to contain polyphenols, some minerals and minor constituents etc. The ethanol was removed by distillation and condensation and the remaining aqueous concentrate was freeze dried to produce a polyphenol powder (PP1).

Step 6: In a further embodiment, eluant E2 was then passed through a 0.5 kDa ultrafiltration membrane and the retentate (R2) was diafiltered. The recovered product contained polyphenols and was concentrated by freeze drying to generate a powder (PP2).

Step 7: The eluant E1 was passed through a 0.5 kDa ultrafiltration membrane, diafiltered and the retentate R3 collected. The retentate R3 was then concentrated by evaporation generating a polyphenols rich liquid PL1 (which could be used for spraying onto sugar to enrich the antioxidant content and manufacture a low GI sugar according to WO 2005/117608), or alternatively fully dried to produce a powder enriched in polyphenols PP2. The 0.5 kDa permeate P2 was collected and concentrated to recover a sugar syrup SY1 enriched in polyphenols, antioxidants and minerals.

Step 8: In another embodiment the material passing through the initial ceramic or stainless steel membrane was treated on a 0.5 kDa membrane producing a retentate that was diafiltered to produce R3. This retentate was found to contain between 80 to 90% of the original polyphenols and antioxidant from the molasses and 60 to 90% of the sucrose but significantly depleted in fructose, glucose and monovalent cations. This retentate was concentrated by evaporation and also could be used for spraying onto sugar to enrich the antioxidant content and manufacture a low GI sugar according to WO 2005/117608, or alternatively fully dried to produce a powder enriched in polyphenols PP2. The permeate from this process had a composition very similar to that shown for SY1.

Results

TABLE 1

Composition of Syrup from 30 kDa membrane permeate (P1)

| Component | Concentration |
| --- | --- |
| Sucrose | 420-480 g/litre |
| Glucose | 100-140 g/litre |
| Fructose | 100-140 g/litre |
| Polyphenols | 12-16 g/CE/litre |
| Antioxidants | 4-5.5 g/GAE/litre |
| Calcium | 2864 mg/l |
| Magnesium | 1510 mg/l |
| Potassium | 12895 mg/l |
| Sodium | 194 mg/l |

Typically the monosaccharides, glucose and fructose constitute between 25 and 35% of the total sugars of the 30 kDa recovered fractions and exist in a ratio of 68:16:16 (average) for sucrose, glucose and fructose. This ratio is similar to that which occurs in the original molasses but is significantly reduced in colour (about 27 to 30%). The levels of calcium and magnesium are also significantly reduced to that of the original molasses. Only 40-50% of the original molasses polyphenols are recovered in this syrup but they are in a different range and profile (being smaller) than those found in the original molasses.

TABLE 2

Composition of Syrup form 0.5 kDa retentate (PL1)

| Component | Concentration |
|---|---|
| Sucrose | 480-520 g/litre |
| Glucose | 80-120 g/litre |
| Fructose | 80-120 g/litre |
| Polyphenols | 16-25 g/CE/litre |
| Antioxidants | 5-9 g/GAE/litre |
| Calcium | 2003 mg/l |
| Magnesium | 1118 mg/l |
| Potassium | 8002 mg/l |
| Sodium | 114 mg/l |

The monosaccharides, glucose and fructose represent between 20 and 30% of the total sugars in the 0.5 kDa retentate PL1.

TABLE 3

Composition of Syrup from 0.5 kDa permeate (SY1)

| Component | Concentration |
|---|---|
| Sucrose | 80-120 g/litre |
| Glucose | 280-320 g/litre |
| Fructose | 280-320 g/litre |
| Polyphenols | 12-15 g/CE/litre |
| Antioxidants | 3.5-7 g/GAE/litre |
| Calcium | 560 mg/litre |
| Magnesium | 333 mg/litre |
| Potassium | 6526 mg/litre |
| Sodium | 98 mg/litre |

The monosaccharides, glucose and fructose represent between 80 and 88% of the total sugars in SY1. It is evident from these results, that a high glucose and fructose sugar syrup can be extracted from the molasses. The method of the invention thus enables the production of a valuable sugar syrup which can be used in food products and which obtains further value from a waste product.

In an alternative process steps 4 and 5 were omitted, and the 30 kDa permeate (PI) was treated as per step 6 above.

Conclusion

This example clearly demonstrates that a difficult feedstock, such as molasses, can be fractionated by membrane filtration and ion exchange chromatography in order to produce fractions that are both rich in polyphenols and antioxidants in association with varying levels of mono and disaccharides and mono and divalent cations.

By the combination of membrane filtration using 30 kDa and 0.5 kDa membranes, crude molasses from cane or beet can be fractionated into sugar syrups differing in the composition of sucrose, glucose, fructose, minerals, mono and divalent cations and anions such as Cl, $SO_4$, $PO_4$, organic acids (eg: cis and trans aconitic, citric and malic acids), and polyphenols (phenolic acids, flavonoids, anthocyanins, anthocyanidins etc).

These syrups can be used individually or blended to produce a range of functional sweeteners rich in minerals and polyphenols (antioxidant activity) for use in a wide range of food systems. Using membrane filtration of molasses, products with reduced mineral content free of large particulate matter can be used as feedstock for further fractionation on resins typically used for ion exchange and hydrophobic chromatography. Such feedstock improve the performance (less poisoning and longer usage life) of these resins. Thus further refined and differentiated sweetener syrups and high polyphenol powders can be produced which have wide application in food systems and for use as nutriceuticals.

Example 2

As an example of how the syrups can be blended to produce a different functional sweetener syrup (mono and disaccharides, mono and divalent cations), four parts of the permeate from the 30 kDa filtration and one part of the permeate from 0.5 kDa filtration from Example 1 were mixed to produce a sweetener with a sucrose, glucose, fructose ratio of 5:2:2 compared to the original 30 kDa permeate (ratio 68:16:16) and original 0.5 kDa permeate 1:3:3. Such mixtures will also produce different levels of polyphenols, antioxidants and minerals and will vary in their colour intensity as measured by the absorbance at 420 nm.

Example 3

The 0.5 kDa retentate from Example 1 contained between 80 to 90% of the original polyphenols and antioxidant activity found in the molasses feedstock. After this retentate was concentrated to a polyphenol content of between 20 and 50 g of CE (catechin equivalents)/l, it was sprayed onto the surface of sugar crystals to produce a low GI sugar.

Example 4

The process according to the second aspect of the present invention was applied to molasses to illustrate the fractionation capabilities of different membranes.

Methods

The membrane filtration plant (approximate dimensions 1200 mm×1200 mm×1600 mm high) was supplied by GEA Liquid Technologies Australia. The unit was equipped with a stainless steel membrane (pore size 0.1 μm) and a housing to accommodate spiral-wound membranes (970 mm×98 mm dia.). The spiral-wound membranes (Syndner 3838) had pore sizes of 0.5, 1.0 and 30 kDa. A spiral-wound reverse osmosis membrane (Dow-Filmtech 3838) was also used.

Deionised water supply: Deionised water was provided by an ion exchange system hired from IBC Water and transported from Brisbane. The tri-bed system consisted of a pre-filter and three ion exchange cylinders connected in series: cation, anion and mixed cation/anion exchangers. The cylinders were connected to the mains water supply and deionised water flowed directly to the MF plant.

Molasses: Hot molasses (70-80° C.) was obtained directly from a production tank and was mixed with an equal volume of deionised water. This diluted molasses (80 l) was adjusted to pH 7.5 with 5 M NaOH (900 ml) and heated at 80° C. for 20 min in aluminium cans. The MF plant was preheated to 80° C. with water which included an added volume of about 15 l and a hold-up volume of about 25 l. The pH-adjusted molasses was then circulated through the plant at 75-80° C. before pre-filtration through a 0.1 μm stainless steel membrane. Based on an estimated density of 1.3 g/ml for hot molasses and 40 l water in the plant, the estimated concentration of molasses applied to the pre-filter was about 43% (w/v).

Group 1 Trials

Prefilter 0.1 μm: Diluted molasses (approx 43% (w/v)) was pre-filtered through a 0.1 m stainless steel membrane at 70° C.

using a feed pressure of 1 Bar and a recirculation pressure of 3 Bar.

Nanofiltration 0.5 kDa: The permeate from the 0.1 μm pre-filter was applied to a spiral-wound membrane with a pore size of 0.5 kDa. The filtration was carried out at 40° C. using a feed pressure of 20 Bar and a recirculation pressure of 21 Bar. The retentate from this run was diafiltered with 60 l of deionised water and stored frozen for possible use in coating raw sugar.

Reverse osmosis: The nanofiltration permeate was passed through a RO membrane at 40° C. using a feed pressure of 25 Bar and a recirculation pressure of 25.5 Bar. The retentate was stored frozen for use in confectionery trials.

Group 2 Trials

The trials from Group 1 were repeated with an additional membrane step using a 30 kDa membrane after prefiltration with the 0.1 μm stainless steel membrane. The run with the 30 kDa membrane was carried out 45° C. using a feed pressure of 4 Bar and a recirculation pressure of 5.5 Bar. Subsequent steps were as for Group 1. Laboratory samples (100 ml) were collected were collected from the feedstock, permeates (final and composite) and retentates. Additional bulk samples were as follows:

composite permeate before diafiltration; PW was the composite permeate collected after diafiltration and PWC was the combination of P2 and PW (FIGS. 2 to 5).

In the figures:

Number before/is membrane cut-off (kDa);/0 is feedstock for that membrane size

P=permeate; R=retentate; W=post water wash; PWC=composite of total permeate and diafiltration permeate.

For 0.1 kDa stainless steel membrane, additional volume (+) includes approximately 15 l added water for preheating, and approximately 25 l hold-up volume in plant.

For non-0.1 kDa stainless steel membranes, additional volume (+) is approximately 25 l hold-up volume in plant.

Analyses: Samples were analysed for the following components: total phenolics, reversed-phase HLPC profiles, antioxidants, mono- and di-saccharides, cis- and trans-aconitic acids, cations/anions, total solids, ash, conductivity, pH, colour ($A_{420}$) and ° Brix. Six samples were analysed for polysaccharides.

Components Analysed and Method of Analysis

| Component | Method |
|---|---|
| Total phenolics | Folin-Ciocalteu colorimetric procedure. Results expressed as g catechin equivalents per l. |
| Polyphenol profile | RP-HPLC, C18 column, (Luna 3 μm, Phenomenex) at 30° C., linear gradient 3-21% acetonitrile for 12 min, 21-60% for 1 min and 21-60% for 3 min. Detection at 214 nm. |
| Antioxidant activity | ABTS substrate. Results expressed as g gallic acid equivalents per l. |
| Mono- and di-saccharides | RP-HPLC, NH2 column at 40° C., isocratic elution with 88% acetonitrile at 1 ml/min for 20 min. R I detection. |
| cis- and trans-Aconitic acids | Ion-moderated partition HPLC, Aminex column HPX-87H (Bio-Rad). Isocratic elution with 0.004 M $H_2SO_4$ at 0.6 ml/min for 40 min at 30° C. UV detection. |
| Total solids | Vacuum oven at 70° C. for 16 h. |
| Ash | Oven dry 100° C. and furnace 550° C. 16 h |
| Conductivity | TPS conductivity meter (model 2102A) fitted with pipette cell. Results expressed as molar NaCl. |
| Colour (A420) | Absorbance at 420 nm on samples diluted in deionised water. |
| ° Brix | ABBE refractometer at 20° C. |
| Polysaccharides | Measurement of soluble polysaccharides. Precipitation of polysaccharides with 100% ethanol, wash with 80% ethanol, digestion of precipitate in 1% sulphuric acid and measurement total reducing sugars by phenol-sulphuric acid at 485 nm with glucose as reference. Results expressed as g polysaccharide per l. |
| Na, K, Ca, Mg, $PO_4$, $SO_4$ | Inductively coupled plasma - optical emission spectroscopy (ICP-OES) on Varian Vista Pro instrument at UQ. |
| Cl | Automated colorimetric analyser (Seal AQ2), EPA Method (EPA-124-A) |

List of Bulk Samples

| Group | Bulk sample | Sample volume (l) |
|---|---|---|
| 1 | 0.5 kDa permeate (P2) | 4 |
| 1 | 0.5 kDa diafiltered retentate | 1, 20 |
| 1 | RO retentate | 10 |
| 2 | 30 kDa permeate (P2) | 4 |
| 2 | 0.5 kDa diafiltered retentate | 1, 15 |
| 2 | RO retentate | 1, 15 |

Samples coded P1 and R1 represented permeate and retentate samples taken at the end of each run. Code P2 represented Filtration parameters: Flow rates, temperatures and pressures were recorded for each membrane. Rejection coefficients (r) for each analyte were calculated as follows:

$r = 1 - C_P/C_R$ where $C_P$=concentration of analyte in permeate; $C_R$=concentration of analyte in retentate at the end of each run.

Percentage permeation data are calculated as $C_P$/concentration of initial feedstock.

Results

Group 1

Plant operation: The flow rate for the stainless steel membrane was very slow (maximum 21 l/h) even though the operating temperature was at 70° C. It was discovered at the end of Group I that the pressure gauges were reading approximately 0.5 Bar too low, resulting in lower flow rates than could have been achieved in the first Group. Pressure levels were adjusted in Group 2. For the 0.5 kDa membrane, flow rates were reasonably high (>40 l/h) for the first 15 min but fell to 20-30 l/h for the remainder of the run. High flow rates (>230 l/h) were achieved with the reverse osmosis membrane.

Composition: Analytical results for membrane filtration streams from Group 1 are shown in FIGS. 2 and 3. The original diluted molasses (50% (v/v)) was not sampled. Based on previous data (eg. phenolics, total solids), the recirculated molasses, prior to pre-filtration with 0.1 μm membrane, has an estimated concentration of approximately 43%. There was little change in most analytes in the pre-filtration permeate. However, colour (A420) was reduced by 13%, with a similar reduction in antioxidant activity. This reduction in antioxidant activity was high compared to Group 2 at 5%. Total phenolics fell by 2% in the permeate, trans-aconitic acid by 8% and polysaccharides by 53%.

For nanofiltration, permeations of sucrose (7%) and divalent ions were low, but monosaccharides were high at 60-80%. Permeation of phytochemicals was 15-17% but aconitic acids were less than 2%. The diafiltered retentate (0.5 RW), which could be used for coating raw sugar, had a Brix of 25° and would need to be concentrated at least twice to have adequate solids content for spray drying. The colour of this retentate was black and visually comparable to molasses. Reverse osmosis treatment of the 0.5 kDa permeate (0.5/PWC) increased the concentration of most analytes 2-3 fold.

Rejection coefficients calculated for P1 and R1 for each membrane are shown in Table 4. A high coefficient (approaching 1) represents low permeation or high rejection by the membrane, while a low coefficient (approaching zero) represents high permeation or low rejection by the membrane. The results in Table 4 generally reflect previous observations regarding composition of the membrane filtration streams.

TABLE 4

Rejection coefficients for membranes used in filtration of molasses (Group 1)

| Component | Membrane | |
|---|---|---|
| | 0.1 μm stainless steel | 0.5 kDa spiral |
| Total phenolics | 0.14 | 0.90 |
| Antioxidants | 0.15 | 0.86 |
| Fructose | −0.12 | 0.57 |
| Glucose | 0.10 | 0.47 |
| Sucrose | 0.02 | 0.95 |
| Total sugars | 0.01 | 0.82 |
| cis-aconitic acid | 0.05 | 0.99 |
| trans-aconitic acid | 0.15 | 0.99 |
| Colour (A420) | 0.35 | 0.99 |
| Brix | 0.08 | 0.79 |
| Sodium (Na) | 0.02 | 0.07 |
| Potassium (K) | 0.03 | 0.10 |
| Calcium (Ca) | 0.22 | 0.80 |
| Magnesium (Mg) | 0.13 | 0.76 |
| Iron (Fe) | 0.32 | 0.99 |
| Chloride (Cl) | 0.20 | −0.51 |
| Phosphate ($PO_4$) | 0.56 | 0.96 |
| Sulphate ($SO_4$) | 0.03 | 0.89 |

RP-HPLC profiles: The RP-HPLC profiles of the membrane filtration streams for Group 1 were measured. Prefiltration through 0.1 μm had no effect on the polyphenol profile of the permeate. However, for the 0.5 kDa membrane, there was no permeation of polyphenols at hydrophobic end of the profile (>8 min). Reverse osmosis provided a concentration of the components observed in the profile of the 0.5 kDa permeate.

Group 2

Plant operation: The starting molasses for Group 2 was sampled from bulk material which had been standing over the weekend when processing was shut down. The composition of this molasses may have differed slightly from that of Group 1. Average flow rates (after 1.5 h) for the 0.1 μm stainless-steel membrane (were about 65% faster than those of Group 1, but were still too slow at 15 l/h for efficient processing. The fine particles of insoluble calcium/magnesium salts produced by heating at pH 7.5 may have contributed to some membrane fouling. High flow rates (>120 l/h) were achieved for the 30 kDa membrane, for the 0.5 kDa membrane (360 l/h at 5 min) and for the RO membrane (350 l/h).

There was a drop in pH in the 30 kDa streams from pH 7.85 for pre-filtered material to pH 5.04 in the recirculated 30 kDa feedstock. As acid detergent was not used in pre-rinsing the 30 kDa membrane, it is assumed that there was a problem with the deionised water supply and that the feedstock was initially recirculated with low pH water. Unfortunately, the pH meter provided malfunctioned in Group 2, so that pH testing of the water supply was not carried out. It is possible that the anion exchange bed may have been exhausted, and failed to neutralise the low pH water from the cation exchanger, in which resin-bound H ions are replaced with hardness cations such as calcium and magnesium.

Composition: The compositional data for Group 2 are shown in FIGS. 4 and 5. As for Group 1, most analytes permeated the 0.1 μm membrane except for polysaccharides (34% permeation). Permeation through the 30 kDa membrane was 60% for polyphenols and antioxidants, 90% for aconitic acids and greater than 72% for individual sugars.

The 0.5 kDa membrane performed somewhat better than in Group 1, with only 10±2% permeation of polyphenols/antioxidants. However, permeation of monosaccharides was surprisingly low at 11-12% compared to 59-80% for Group 1. This may have been due to osmotic effects or the use of low pH feedstock (pH 5.3). Sucrose showed 1% permeation by the membrane, and aconitic acids less than 3% permeation. Monovalent cations (Na, K) also showed less permeation than in Group 1. As expected, divalent ions were largely rejected by the 0.5 kDa membrane. A summary of rejection coefficients for Group 2 is shown in Table 5. The incidence of some negative coefficients is due to anomalous results for permeates or retentates.

(a) RPHPLC Profiles

RP-HPLC profiles of the membrane filtration streams for Group 2 were measured. The 30 kDa permeate showed a notable reduction in the levels of two peaks at the hydrophobic end of the profile (>11 min). As for Group 1, the 0.5 kDa permeate showed a loss of peaks from the hydrophobic region of the profile (after 8 min). Subsequent to this study, an investigation of a lab scale 100 kDa membrane showed a general reduction of peak heights for the permeate, but less reduction at the hydrophobic end than for the 30 kDa membrane. Permeation of antioxidant activity by the 100 kDa permeate (68%) was slightly higher than for the 30 kDa permeate (60%) produced.

TABLE 5

Rejection coefficients for membranes used in filtration of molasses (Group 2)

| Component | Membrane | | |
|---|---|---|---|
| | 0.1 µm SS | 30 kDa spiral | 0.5 kDa spiral |
| Total phenolics | 0.16 | 0.56 | 0.90 |
| Antioxidants | 0.17 | 0.54 | 0.87 |
| Fructose | 0.20 | 0.28 | 0.80 |
| Glucose | −0.15 | 0.50 | 0.80 |
| Sucrose | 0.03 | −0.21 | 1.0 |
| Total sugars | 0.04 | 0.05 | 0.95 |
| cis-aconitic acid | 0.06 | 0.20 | 0.97 |
| trans-aconitic acid | 0.11 | 0.22 | 0.99 |
| Colour (A420) | 0.36 | 0.86 | 0.98 |
| Brix | 0.06 | 0.25 | 0.89 |
| Sodium (Na) | −0.14 | 0.15 | 0.25 |
| Potassium (K) | −0.15 | 0.15 | 0.28 |
| Calcium (Ca) | 0.06 | 0.31 | 0.91 |
| Magnesium (Mg) | 0.06 | 0.25 | 0.93 |
| Iron (Fe) | 0.39 | 0.84 | 0.97 |
| Chloride (Cl) | 0.16 | 0.31 | −4 |
| Phosphate ($PO_4$) | 0.45 | 0.56 | 0.97 |
| Sulphate ($SO_4$) | −0.09 | 0.27 | 0.99 |

Conclusions

Pre-filtering of a 43% (w/v) molasses mix using a 0.1 µm stainless-steel membrane was effective but slow, giving stabilised flow rates of 15 l/h. Most components readily permeated the 0.1 µm membrane except for polµysaccharides.

Nanofiltration (0.5 kDa) adequately rejected phenolics, antioxidant activity, sucrose, aconitic acids and divalent ions when using feedstock from 0.1 µm and 30 kDa membranes. However, permeation of monosaccharides by 0.5 kDa was considerably higher when used after the 0.1 µm membrane than after the 30 kDa membrane.

Ultrafiltration (30 kDa) using feedstock from the 0.1 µm membrane showed satisfactory permeation levels for most analytes, with highest rejection for colour at 420 nm (r=0.86) and iron (r=0.84). Inclusion of a 30 kDa membrane before a 0.5 kDa membrane has the advantages of faster flow rates for subsequent nanofiltration and a reduction of colour in 0.5 kDa retentates. The main disadvantage is the loss of phytochemicals (40%) into the 30 kDa retentate.

Reverse osmosis treatment of the 0.5 kDa permeates increased the concentration of most analytes two to three fold in the retentate.

This example demonstrates that a range of membranes and techniques can be used to produce extracts according to the first aspect of the invention which have a variety of characteristics.

Example 5

Membrane filtration of molasses requires the feedstock to be diluted to 40-60% (w/v) with hot water and pre-filtered or centrifuged to remove the 1-2% (v/v) sediment load. Before proceeding to nanofiltration on a 0.5 kDa membrane, an interim ultrafiltration step is preferred in order to maintain satisfactory flux rates on the nanofiltration membrane and remove polymeric components such as Maillard polymers and polysaccharides. Trials carried out using a 30 kDa spiral-wound membrane after pre-filtration with a 0.1 µm stainless-steel membrane showed high flow rates of 120-150 l/h by the 30 kDa membrane.

The current example investigates whether a 100 kDa membrane offered any advantages in component fractionation compared to a 30 kDa membrane. Specifically, a laboratory scale 100 kDa membrane (VivaFlow 50) was tested for its fractionation capabilities using 40% (w/v) molasses at 50° C.

Methods

Diluted molasses (40% w/v) was centrifuged at 6000 g for 1 h at 10° C. and filtered through a 1.6 µm glass-fibre filter (Whatman GF/A). The diluted molasses (40% w/v) held at 50° C. was filtered through a 100 kDa polyethersulphone membrane (107 mm×84 mm×25 mm, Vivaflow 50, Sartorius) at 1 Bar and 2.5 Bar in separate experiments using new cassettes. An additional run (Run 2) was carried out on a regenerated membrane at 2 Bar following the first trial at 1 Bar.

Analyses: The following tests were carried out on the feedstock, permeates and retentates for each run: total phenolics, antioxidant activity, aconitic acids, polysaccharides, colour (A420) pH, conductivity and HPLC profiles.

Results

Table 6 shows the changes in colour and composition after filtration through Vivaflow 50 crossflow membrane (100 kDa MWCO). Run 1 was carried out at 1 Bar pressure and Run 3 at 2.5 Bar, using new membranes for each run. The lower pressure in Run 1 was to compensate for leaks in tubing connections. Run 2 used a regenerated membrane following Run 1, however, the supplier advised that membrane reuse was not recommended.

TABLE 6

Composition of molasses after membrane filtration on Sartorius Vivaflow 50 cross-flow cassette with molecular weight cut-off 100 kDa.

| Run No | Sample | A420 | Total phenolics (g/l) | A/Ox activity (g/l) | Cis-Aconitic (g/l) | Trans-Aconitic (g/l) | Poly-sacch. g/l | pH | Conduct. (NaCl, M) |
|---|---|---|---|---|---|---|---|---|---|
| 1 | Feed | 34.4 | 8.33 | 2.65 | 1.80 | 6.80 | 10.17 | 5.58 | 0.19 |
| | Permeate | 17.8 | 5.89 | 1.88 | 1.68 | 6.46 | 1.12 | 5.56 | 0.21 |
| | Retentate | 37.1 | 8.42 | 2.59 | 1.83 | 6.89 | 10.64 | 5.57 | 0.20 |
| 2 | Feed | 34.7 | 8.13 | 2.61 | 1.78 | 6.68 | 10.35 | 5.58 | 0.20 |
| | Permeate | 10.0 | 4.91 | 1.59 | 1.58 | 6.04 | 0.72 | 5.57 | 0.21 |
| | Retentate | 37.4 | 8.14 | 2.71 | 1.80 | 6.73 | 11.04 | 5.58 | 0.19 |
| 3 | Feed | 30.3 | 7.19 | 2.29 | 1.53 | 6.03 | 9.25 | 5.64 | 0.19 |
| | Permeate | 11.1 | 4.90 | 1.46 | 1.41 | 5.68 | 0.83 | 5.62 | 0.20 |
| | Retentate | 35.5 | 7.89 | 2.38 | 1.58 | 6.17 | 11.43 | 5.63 | 0.19 |

For Runs 1 and 3 there was a significant loss in colour in the permeates (48% and 63% respectively). Permeation of phenolics and antioxidants for Run 1 was 71%. For Run 3, which was at slightly higher back pressure, permeation of phenolics and antioxidants was 68% and 64%, respectively. Permeation of cis- and trans-aconitic acids for Runs 1 and 3 was high at 92-95%, while polysaccharides was low at 9-11%. Reversed-phase HPLC profiles of the samples were measured for each run. While peak heights were reduced in the respective permeates, there was no loss of any individual peaks in these samples.

Table 7 shows data collected from membrane filtration trials using approximately 43% molasses feedstock. There was little reduction in phytochemicals or aconitic acids after 0.1 μm filtration. Feedstock for the 30 kDa spiral-wound membrane was considerably diluted by the start-up volume of the filtration plant. The estimated dilution (from reduced component levels in the 30 kDa feedstock) was 1.57 times. This gives an estimated polysaccharide level in the 30 kDa feedstock of 2.2 g/l. Colour loss in the permeate was higher than that for the 100 kDa membrane. Permeation of phytochemicals through the 30 kDa membrane was 60% for phytochemicals, 89% for aconitic acids and 95 for polysaccharides. In these trials, the notable pH drop to 5.0 in the 30 kDa feedstock was possibly due to a failure by the anion exchange cartridge.

TABLE 7

Composition of molasses after membrane filtration through a 0.1 μm stainless-steel (SS) membrane and a 30 kDa spiral-wound membrane.

| Sample | A420 | Total phenolics (g/l) | A/Ox activity (g/l) | Cis-Aconitic (g/l) | Trans-Aconitic (g/l) | Poly-sacch. (g/l) | pH | Conduct. (NaCl, M) |
|---|---|---|---|---|---|---|---|---|
| Pre 0.1 μm SS membrane | 51.4 | 6.88 | 2.42 | 1.59 | 7.02 | 10.3 | 8.1 | 0.21 |
| Permeate from 0.1 μm SS membrane | 40.9 | 6.84 | 2.31 | 1.70 | 6.73 | 3.5 | 7.7 | 0.22 |
| Feedstock for 30 kDa | 20.2 | 4.6 | 1.46 | 1.03 | 4.24 | N/T (est. 2.2) | 5.0 | 0.19 |
| Permeate from 30 kDa | 4.8 | 2.76 | 0.88 | 0.93 | 3.76 | 0.20 | 5.3 | 0.19 |

Conclusions

This example demonstrated that the permeation of total phenolics and antioxidants using a 100 kDa membrane (64-71%) was slightly higher than that of a 30 kDa membrane (60%). The permeations of aconitic acids (89-95%) and polysaccharides (9-11%) were similar for both membranes, that is, the 100 kDa membrane gave slightly higher permeation of phytochemicals (phenolics and antioxidants) but similar permeation of aconitic acids and polysaccharides. Colour reduction was greater with the 30 kDa membrane.

Accordingly, a 100 kDa membrane is recommended for improved permeation of phytochemicals but offers no advantage over a 30 kDa membrane for removal of polysaccharides and colour.

Example 6

This example investigates the use of gel permeation to produce extracts according to the first aspect of the invention.

Methods

Preparative gel filtration on a Bio-Gel P-2 column was used to fractionate diluted molasses (50% w/v) in the molecular weight range of 100 to 1800 daltons (Da). Five molecular weight fractions from six chromatography runs were pooled and freeze dried. The fractions were analysed for antioxidant activity, total phenolics, HPLC profile and sugars.

The molasses was diluted to 50% (w/v) in gel filtration buffer (20 mM ammonium formate pH 5.0 containing 10% acetonitrile) and centrifuged at 6000 g for 1 hour at 10C. The supernatant was filtered through a 1.6 μm GF/A filter (Whatman) and frozen in 30-ml aliquots at −80° C. for use in gel filtration chromatography.

Gel Filtration

A glass column (26 mm×1000 mm) was packed with Bio-Gel P-2 (BioRad, USA) to a bed height of 910 mm at a flow rate of 60 ml/h. The bed was equilibrated at 30 ml/h at room temperature in 20 mM ammonium formate buffer pH 5.0 containing 10% acetonitrile. Diluted molasses (20 ml of 50% w/v) was applied to the column and 5-ml fractions were collected. Six gel filtration runs were carried out on a total of 120 ml of diluted molasses. Fractions from the first three runs were analysed for colour ($A_{420}$), total phenolics and antioxidant activity. For the last three runs antioxidant assays were omitted. Fraction volumes were determined gravimetrically by weighing approximately 20 tubes per run and determining the average fraction volume using a density of 1 g/ml.

The gel filtration column was calibrated with three standards: sucrose (360 kDa), NADH (663 kDa) and vitamin B12 (1355 kDa). The distribution coefficient (KDa) for each standard was calculated as KDa=Ve-Vo/Vt-Vo. The void volume was determined with bovine serum albumin. The fractionation range of Bio-Gel P-2 is 100-1800 Da (BioRad).

Lyophilised bulk fractions: For each gel filtration run, individual fractions were pooled into five major fractions according to profiles of colour ($A_{420}$), total phenolics and antioxidants. The pooled fractions for each run are shown in Table 15.

TABLE 8

List of Pooled Fractions for each Run

| Run No | Fraction volume (ml) | Pooled fractions | | | | |
|---|---|---|---|---|---|---|
| | | Pool 1 | Pool 2 | Pool 3 | Pool 4 | Pool 5 |
| 1 | 4.88 | 34-50 | 51-66 | 67-82 | 83-100 | 101-120 |
| 2 | 4.74 | 35-54 | 55-72 | 73-83 | 84-104 | 105-120 |
| 3 | 4.95 | 35-52 | 53-68 | 69-79 | 80-100 | 101-120 |
| 4 | 4.69 | 35-53 | 54-71 | 72-81 | 82-100 | 101-120 |
| 5 | 4.52 | 37-56 | 57-76 | 77-87 | 88-103 | 104-120 |
| 6 | 4.71 | 35-51 | 52-71 | 72-81 | 82-99 | 100-120 |
| Total vol. (ml) | | 447 | 435 | 270 | 452 | 470 |

After six gel filtration runs, the six samples within each pool (Pools 1-5) were combined. A 10-ml sample was taken from each final pool and the remainder freeze dried.

Colour ($A_{420}$): Gel filtration fractions were diluted with ultrapure water (Arium Model 611, Sartorius) and absorbance was read at 420 nm on a Heliosλ (Unicam) spectrophotometer.

Total phenolics: Total phenolics were determined by a Folin-Ciocalteu colorimetric procedure (Kim et al., 2003). To 50 µL of diluted sample in a 75-mm test tube was added 650 µL of deionised water. Undiluted Folin-Ciocalteu reagent (50 µL) was added to each tube. The solution was mixed and allowed to stand for 5 min at room temperature. Finally 500 µL of 7% $Na_2CO_3$ was mixed with the reaction solution and the absorbance at 750 nm was read after 90 min at room temperature. The total phenolics content was expressed in µg catechin equivalents per ml of undiluted sample. Catechin standards were prepared in the range of 0-250 µg/ml.

Antioxidant activity: Initially, a substrate containing equal volumes of 14 mM ABTS (2, 2'-azinobis (3-ethylbenzothiazoline-6-sulfonic acid) diammonium salt) and 4.9 mM potassium persulphate was prepared and stored overnight in the dark at room temperature. Prior to the assay, this solution was diluted about 60-fold with ultrapure water and adjusted to give an absorbance at 734 nm of 0.99-1.01. ABTS substrate (1 ml) was preincubated in 75-mm test tubes at 26° C. for 5 min in a water bath and 50 uL of sample or standard was added. The solution was mixed and held at 26° C. for 45 min when absorbance was measured at 734 nm. Antioxidant activity was expressed in µg gallic acid equivalents per ml of undiluted sample. Gallic acid standards were prepared in the range 0-25 µg/ml.

RP-HPLC profiles: Qualitative fingerprints of molasses extracts were obtained on a Shimadzu system equipped with a system controller (Model SCL-10AVP), dual pumps (Model LC10-AD), photo diode array (PDA) detector (Model SPD-M10AVP) and Class Vp version 6.14 software for data acquisition and analysis. Samples (10 µl) were eluted at 30° C. on a 30×4.6 mm Luna 3 µm C18(2) column (Phenomenex). The flow rate was 1.5 ml/min. Mobile phases were: phase A, 0.1% (v/v) trifluoroacetic acid (TFA) in water and phase B, 60% acetonitrile in 0.085% TFA. The gradient profile was 5-35% B for 12 min; 35-100% B for 1 min and 100% B for 3 min, 100-5% B for 0.3 min and 5% B re-equilibration for 4.7 min. Eluted peaks were detected by a PDA detector measuring the absorbance spectrum from 200-400 nm at 4 nm wavelength steps and individual channels at 214, 254, 280, 340 and 400 nm, with the 214 nm chromatogram routinely reported. Gel filtration samples were prepared from five lyophilised pools and contained equal concentrations of total phenolics (1 mg catechin equivalents per ml). The sample of molasses used for gel filtration contained 2 mg CE/ml.

Sugar analysis: Mono- and disaccharides were analysed by reversed-phase HPLC using a Shimadzu system fitted with a system controller (Model SCL-10AVP), pump (Model LC-10ADVP), refractive index detector (Model RID-10A) and Class Vp 6.12 software. Samples (10 µl) were injected into a 5-µm LC-NH2 Supelcosil column (250 mm×4.6 mm, Phenomenex) operated at 40° C. The mobile phase was 85% acetonitrile and the flow rate was 1 ml/min. Samples were eluted isocratically for 20 min and were analysed in duplicate. Standard curves for glucose, fructose and sucrose were prepared in the range 0.3 to 1.2 mg/ml, using four standard solutions containing the same gravimetric concentrations of the respective sugars. Triplicate injections were made for each standard solution.

SDS-PAGE: Electrophoresis by SDS-PAGE was performed on 12% acrylamide gels using the mini-Protean II slab-gel system (BioRad). Lyophilised samples from gel filtration were dissolved in water (200 mg/ml) and 30 ul was digested in an equal volume of loading buffer. A volume of 15 ul (1.5 mg of solids) was loaded onto the gel. Electrophoresis was stopped when the bromophenol blue dye front reached the bottom of the gel. The gel was stained in 0.25% Coomassie Blue and scanned on a desktop scanner (Scanjet 5400C, Hewlett Packard).

Results

Calibration of Bio-Gel P-2: A calibration curve for determining molecular weights on the Bio-Gel P-2 column was prepared.

Gel filtration Profiles

Figure 7:
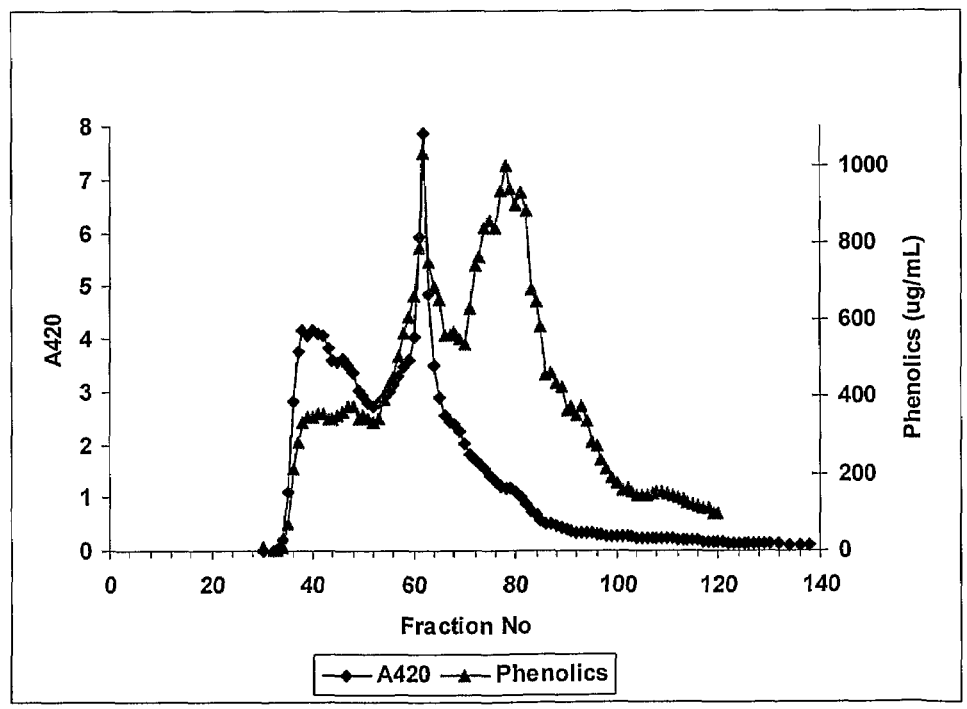
FIG. 7 shows the gel filtration of molasses on Bio-Gel P-2 showing A420 and total phenolics for Run 3 from Example 6.

The gel filtration profiles for colour ($A_{420}$), antioxidants and total phenolics from molasses (Run 3) are shown in FIGS. 6 and 7. The $A_{420}$ colour profile showed a peak near the void volume of the column and a sharp peak at fraction 62 (MW 832 Da). The absorbance then decreased gradually to baseline. Profiles of antioxidants and total phenolics closely coincided with each other. The first two antioxidant/phenolic peaks coeluted with the $A_{420}$ peaks. However, a broad antioxidant/phenolic peak at fraction 80 (MW 352) did not correspond to a colour peak. This peak, comprising fractions 69-100 has a molecular weight range of 135-599 Da and may be a mixture of low colour flavonoids and polyphenolic acids.

Figure 8:
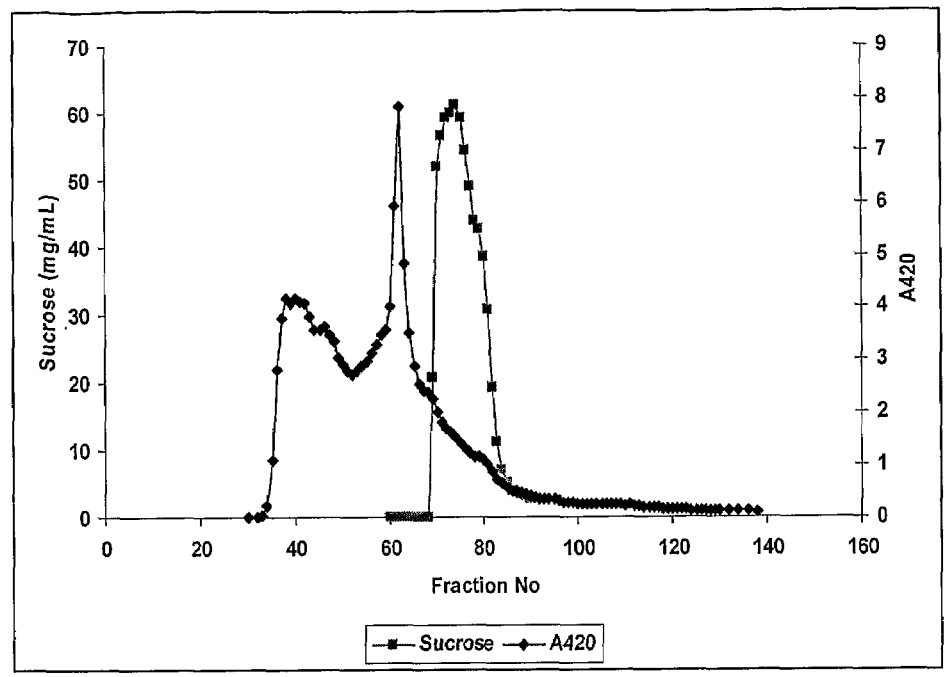
FIG. 8 shows the gel filtration of molasses on Bio-Gel P-2 showing A420 and sucrose for Run 3 from Example 6.
Figure 9:
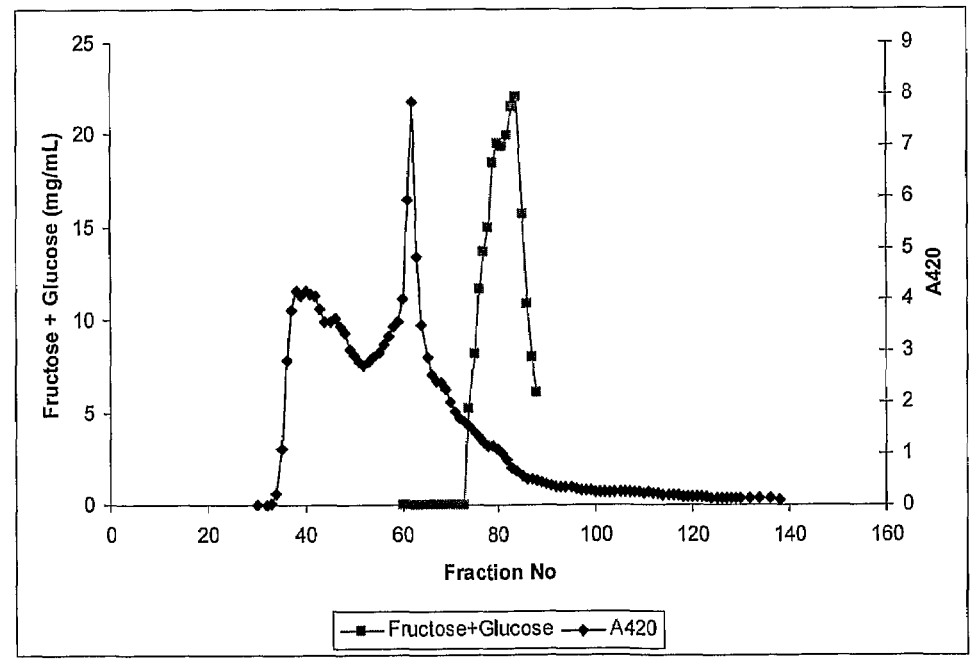
FIG. 9 shows the gel filtration of molasses on Bio-Gel P-2 showing A420 and glucose+fructose for Run 3 from Example 6.

Profiles of sucrose and monosaccharides (glucose+fructose) are shown in FIGS. 8 and 9 respectively. The column was capable of partially resolving sucrose and monosaccharides. Sucrose was eluted on the leading edge of the antioxidant peak (pre fraction 80) and monosaccharides on the tailing edge (post fraction 80). Hence the low colour antioxidant peak contains all the simple sugars of molasses.

For membrane filtration applications, where a low colour antioxidant product is required, it would be necessary to target the molecular weight region below 600 Da. Separation of the antioxidants from the sugars should be possible by ion exclusion chromatography.

Bulk Gel Filtration Pools

Figure 10:
FIG. 10 is a photograph of the fractionation of molasses obtained on Bio-Gel P-2 (Pools 1-5 from Example 6).
Figure 11:
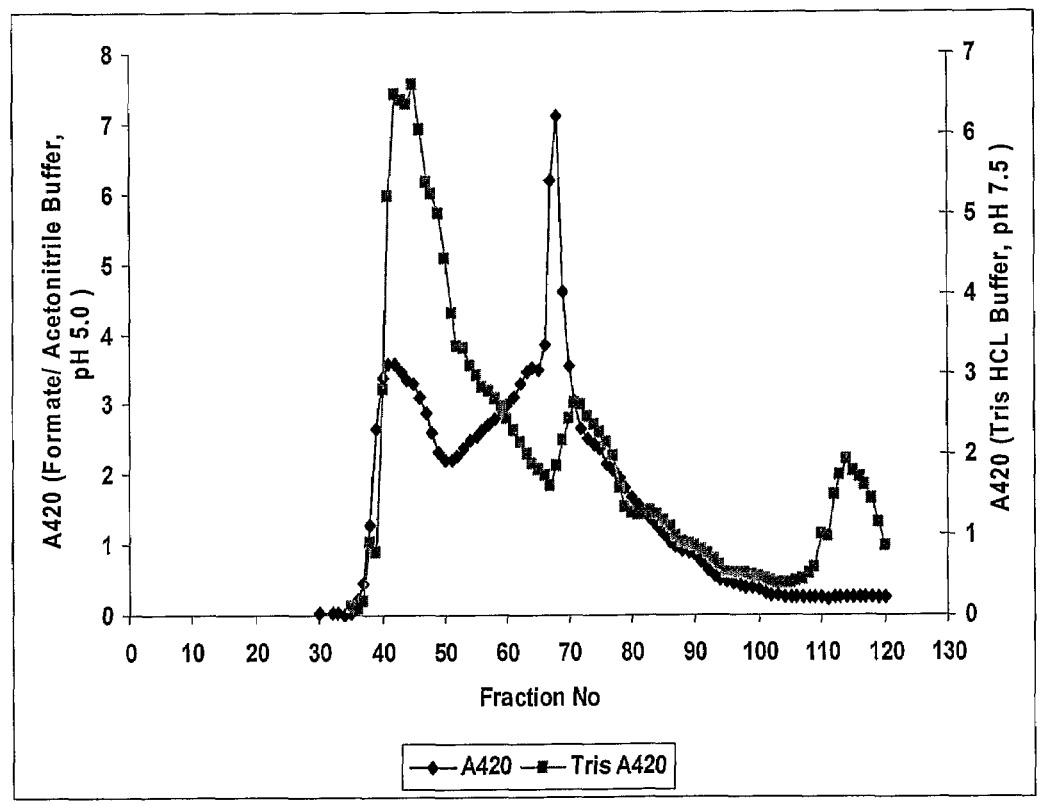
FIG. 11 shows the gel filtration of molasses on Bio-Gel P-2 showing A420 profiles using formate/acetonitrile buffer pH 5.0 and Tris HCl buffer pH 7.5 from Example 6.

The five pools for each of the six gel filtration runs were thawed and combined before freeze drying. FIG. 10 shows the colours of the combined pools (Pools 1-5) prior to freeze drying. Pools 1 and 2 were both very dark; Pool 1 was slightly turbid and Pool 2 was translucent. Pools 3-5 showed decreasing colour from light brown to pale yellow.

Table 9 shows the composition of the combined pools before freeze drying and the average molecular weight range for each pool. From the mass calculations, the low colour antioxidant/phenolic peak (FIGS. 6 and 7) contained 49% of the antioxidant activity and 50% of the phenolics, respectively. The dark-coloured peak eluting at the void volume (Pool 1) contained 14% of the antioxidant activity, and the dark-coloured sharp peak (Pool 2) contained 28%. Recovery of antioxidant activity from the column was 70%.

TABLE 9

Composition of combined pools from gel filtration on Bio-Gel P-2 prior to freeze drying.

| Component | Pool 1 | Pool 2 | Pool 3 | Pool 4 | Pool 5 |
|---|---|---|---|---|---|
| Volume (ml) | 437 | 425 | 260 | 442 | 460 |
| Total solids (g/100 ml) | 0.56 | 1.36 | 7.3 | 3.24 | 0.15 |
| Total phenolics (μg CE/ml) | 324 | 555 | 761 | 550 | 141 |
| Antioxidant activity (μg GAE/ml) | 92 | 183 | 229 | 173 | 49 |
| Fructose (mg/ml) | BDL | BDL | 4.0 | 5.1 | BDL |
| Glucose (mg/ml) | BDL | BDL | 5.1 | 4.2 | BDL |
| Sucrose (mg/ml) | BDL | 0.70 | 50 | 12 | BDL |
| Total solids (g) | 2.45 | 5.78 | 18.98 | 14.32 | 0.69 |
| Total phenolics (mg CE) | 142 | 236 | 198 | 243 | 65 |
| Antioxidants (mg GAE) | 40 | 78 | 60 | 76 | 23 |
| Average molecular wt range | >1800-1444 | 1377-636 | 604-373 | 356-156 | 150-65 |

Composition of load molasses: Total solids=35.6 g/100 ml; $A_{420}$=43.7;

Total phenolics=10340 μg/ml; Antioxidant activity=3390 μg/ml.

Total volume of molasses for 6 runs=120 ml.

Table 10 shows the composition of combined pools after freeze drying. With respect to physical properties, Pool 1 was a fluffy product and differed considerably from Pool 2 which had a hard crunchy texture. Pools 3 and 4 were crunchy and hygroscopic, and contained 71% and 64% sugars, respectively. Pool 5 was dark and sticky and was difficult to remove from the drying tray resulting in significant loss of product. On a solids basis (mg GAE/g of solids), there was a significant loss in antioxidant activity on freeze drying of Pool 2 (26%) and Pool 5 (34%).

TABLE 10

Composition of combined pools from gel filtration on Bio-Gel P-2 after freeze drying

| Component | Pool 1 | Pool 2 | Pool 3 | Pool 4 | Pool 5 |
|---|---|---|---|---|---|
| Weight of dried product (g) | 2.62 | 5.23 | 18.17 | 13.74 | 0.5 |
| Total phenolics (g/100 g) | 5.60 | 4.1 | 0.99 | 1.70 | 5.42 |
| Antioxidant activity (g/100 g) | 1.6 | 0.99 | 0.29 | 0.55 | 2.1 |
| Fructose (g/100 g) | BDL | BDL | 5.0 | 16 | BDL |
| Glucose (g/100 g) | BDL | BDL | 7.1 | 14 | BDL |
| Sucrose (g/100 g) | BDL | 6.7 | 59 | 34 | BDL |
| Total phenolics (mg CE) | 147 | 214 | 180 | 234 | 27 |
| Antioxidants (mg GAE) | 42 | 52 | 53 | 76 | 11 |
| Texture | Fluffy | Crunchy | Crunchy | Crunchy | Tacky |
| Colour | Black | Black | Light brown | Light brown | Black |

Composition of load molasses: Total solids=35.6 g/100 ml; $A_{420}$=43.7;

Total phenolics=10340 μg/ml; Antioxidant activity=3390 μg/ml.

Total volume of molasses for 6 runs=120 ml.

RP-HPLC profiles: Reversed phase HPLC profiles of lyophilised gel filtration pools (profiles b-f) were examined. There were notable differences between all profiles which could be used to characterise the pools. Pool 1 showed a gradual rising profile with only one minor peak. Presumably this sample contains heterogeneous polymeric material which could not be resolved to individual peaks by the HPLC column. Pool 2 represents the molecular weight range 636-1377 Da and includes the sharp peak of dark brown material. This pool showed the most hydrophilic material eluting at less than 1 min, and a number of well-resolved peaks on the gradient. Pools 3 and 4 represent the low-colour antioxidant peak and showed considerable differences between their respective profiles. Pool 5 showed a range of peaks which could represent low molecular weight phenolic acids and a higher molecular weight compounds that have been weakly bound to the column and were not eluted according to their molecular weights. The proportion of hydrophilic material in this pool was low resulting in greater peak heights in the hydrophobic region of the profile. The molasses load sample enables some peaks to be matched up to certain molecular weight ranges in the pools, as well as showing which molasses peaks are weakly bound to the gel and eluted in Pool 5. All samples exhibited a significant peak at 14.5 min which is not relevant to the chromatography, and represents an acetonitrile flush to remove all bound material from the column at the end of the run. Interestingly, this peak which represents the more hydrophobic compounds in molasses, decreased with molecular weight of the pools.

SDS-PAGE: Denaturing electrophoresis of the lyophilised pools was used to detect protein material in the extracts. No protein bands were apparent above 14 kDa in the extracts. In Pool 1 (Lane 2) light staining was observed close to the dye front, but it is uncertain if this is stained protein or residual Coomassie Blue from an uneven dye front. Detection of low molecular weight polypeptides (<10 kDa) would require a 16% gel with a Tris-Tricine buffer.

Conclusion

The gel filtration profiles showed that dark molasses colorants measured at 420 nm were eluted in the void volume of the column (>1800 Da) and at 832 Da. Antioxidant activity and total phenolics co-eluted with these two colour peaks. A broad antioxidant/phenolic peak was eluted between 135 and 599 kDa, but was not associated with a colour peak. This antioxidant peak contained all the sucrose and monosaccharides. It comprised 49% of the eluted antioxidant activity and 50% of the total phenolics. Consequently, removal of the dark colorants of molasses would approximately halve the antioxidant activity of the product. The dark-coloured polymeric material eluting near the void volume comprised 14% of the eluted antioxidant activity.

The quantities of lyophilised gel filtration pools varied from 0.5 g to 18 g, with high masses obtained for the two pools containing sugars. Recovery of antioxidant activity was greater than 92% in three of the lyophilised pools, but significant losses in antioxidant activity was found in Pools 2 and 5.

HPLC fingerprints of the lyophilised pools showed some distinct differences which could be used to characterise the samples. Protein analysis by denaturing polyacrylamide gel electrophoresis showed an absence of protein material above 14 kDa in all lyophilised samples. Pool 1 showed a trace of a protein stain near the dye front. This could be bound protein associated with hydrolysable tannins The lyophilised samples will be analysed subsequently for polysaccharides and polyphenol characterisation, and for their ability to inhibit gut enzymes.

The example demonstrates that the colour profiles obtained by the gel filtration of molasses were dependent on the pH and/or composition of the buffer and that a less coloured high antioxidant extract according to the invention can be produced. At pH 7.5, most of the dark colour was eluted at the void volume, while at pH 5.0, a second dark-coloured peak was observed at lower molecular weight. The pH 5.0 buffer contained 10% acetonitrile which could have contributed to a change in the permeation properties of the gel.

Such a lower colour high antioxidant extract will be useful as an additive to foods to reduce GI, reduce carcinogenicity or change body composition without interference with the colour or organoleptic properties of the food. Further, a lower colour extract according to the invention is useful in pharmaceutical applications, especially where colour and bitterness are important issues.

Example 7

The levels of 16 phenolic compounds were determined in aqueous acidic and basic fractions of two samples of molasses extracts according to the first aspect of the present invention, and one sample of sugar sprayed with molasses extract according to the first aspect of the present invention. The phenolic compounds were isolated by ethyl acetate extraction from the samples.

Three samples were received for evaluation. The details of each sample are shown below.

Sample 1: XAD bound fraction from molasses (powder)
Sample 2: MF purified fraction from molasses (0.5 kDa retentate from 30 kDa permeate, powder) [MFP]
Sample 3: Low GI sugar Methods Sample preparation—Reverse Phase Solid Phase Extraction (SPE) clean-up: A $C_{18}$ SPE cartridge (4 ml, 600 mg; Alltech Associates, Deerfield, Ill.) was conditioned with methanol (3 ml) and formic acid (0.05%, 6 ml). XAD bound fraction (Sample 1) (189.5 mg) was dissolved into aqueous formic acid (0.05%, 10 ml) in a volumetric flask. An aliquot of this solution (3 ml) was loaded onto the cartridge, washed with formic acid (0.05%, 5 ml) and was eluted with aqueous methanol (20% followed by 60% and 100%, 5 ml each) resulting in three fractions. Most brown colour was observed to elute in the 60% aqueous methanol fraction.

Solvent extraction: An aliquot of each sample (~200 mg) was dissolved in water (10 ml) that had been acidified (pH 1.6) or basified (pH 9.6). Methyl-4-formyl benzoate (7.4 µg) was added to each solution as an internal standard (ISTD). The mixtures were then extracted with ethyl acetate (2×10 ml), the solvent was evaporated under vacuum (40° C.) and the mixtures were reconstituted in aqueous formic acid (0.1%, 5 ml) before subjected to HPLC and LC/MS analysis.

HPLC analysis: HPLC was carried out using a Shimadzu system equipped with two high-pressure LC-10ADVP pumps, a SIL-10ADVP autosampler (250 µL sampling loop), a CTO-1-ADVP column oven and a SPD-M10ADVP photo-diode array detector (Shimadzu Inc., Rydalmere, NSW, Australia). The column used for the separation of the polyphenols was a Luna $C_{18}$, (4.6 mm i.d×250 mm length, 5 µm particle size, Phenomenex, Lane Cove, NSW, Australia). The mobile phases used for the separation were 2% TFA in water (A) and 0.5% TFA in acetonitrile:water (1:1) (B) under a flow rate of 1 mlmin$^{-1}$. Analytes were eluted using a linear gradient: 20-50% B over 20 min., 50-100% B over 10 min remained at 100% B for another 10 min. Detection was carried out at 280, 320 and 370 nm. Analytes were identified by comparison of their elution time (and characteristic m/z fragments from LC/MS analysis, Table 2) with those of authentic standards (Sigma-Aldrich, Castle-Hill, NSW, Australia).

LC-MS analysis: LC-MS analysis was carried out on a Quantum TSQ mass spectrometer (ThermoFinnigan, NSW, Australia) equipped with a quaternary solvent delivery system and an autosampler. An aliquot (10 µl) of each extract investigated was chromatographed on a Ultracarb™ analytical column (2.1×150 mm, 5 µm particle size), (Phenomenex, NSW, Australia) which was heated to 30° C. in an oven. The mobile phase consisted of 0.5% formic acid in water (A) and 0.5% formic acid in acetonitrile/water (1:1)(B) at the rate of 300 µl/min. A linear gradient was used (20% B to 100% B over 19 min). Ions were generated using an electrospray source in the negative mode under conditions set following optimisation using a solution of chlorogenic acid.

Results

As explained below, the XAD sample was found to contain significantly higher levels of 16 selected phenolic compounds than the MFP and low GI sugar sample. Several additional constituents, including tricin- and diosmetin-glycosides, were tentatively identified in the XAD sample by LC-MS/MS experiments.

Extraction approach: An SPE-based extraction of the polyphenolic fraction was initially carried out. As expected from previous findings the 60% methanol fraction contained more polyphenolic compounds (based on UV absorption at 280, 320 and 370 nm) than the other two methanol fractions. However, the UV traces from the SPE extractions exhibited low signal-to-noise ratio.

Figure 12:
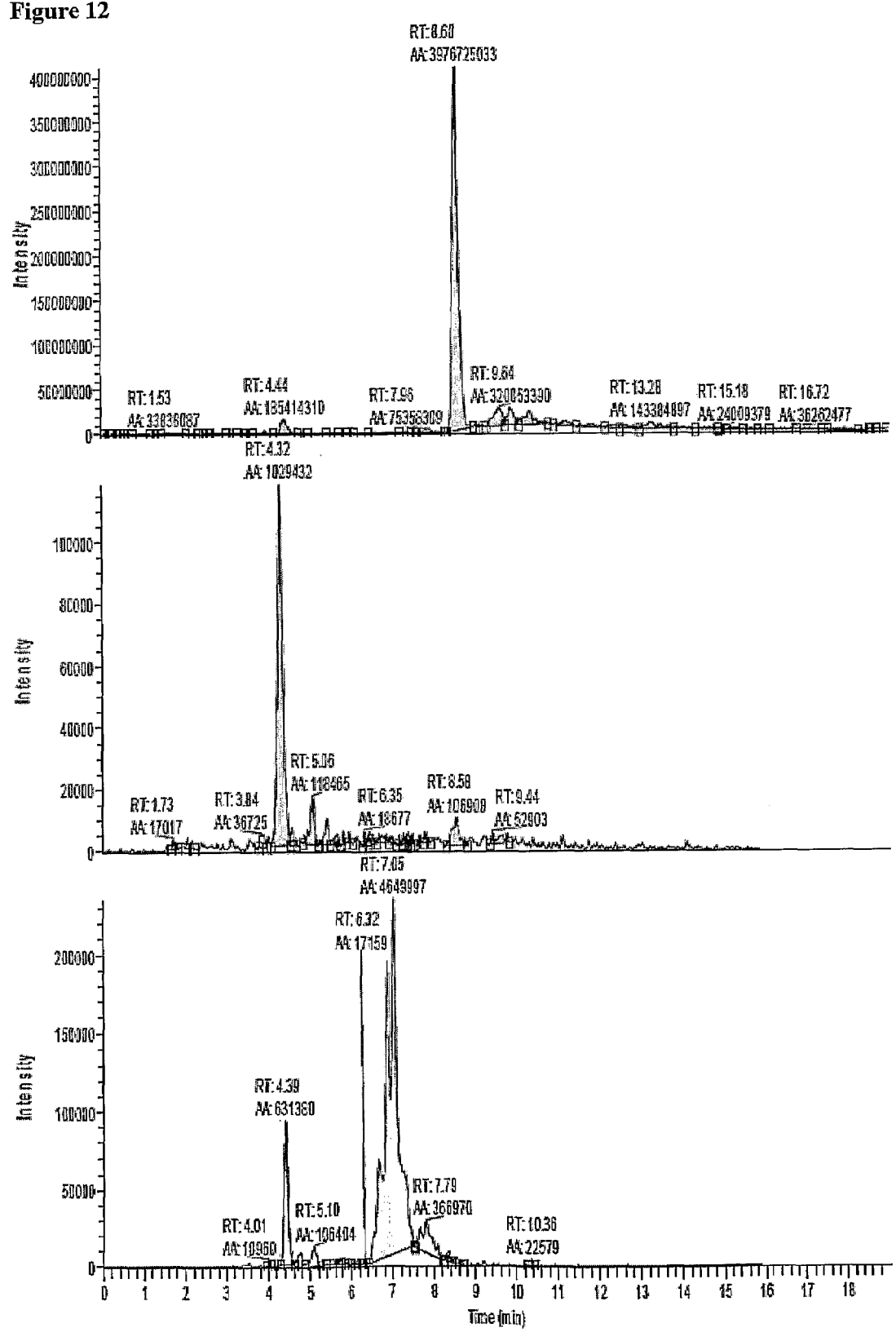
FIG. 12 shows the comparison of the UV traces of the extracts from the ethyl acetate extraction (acidic fraction) (black trace) and the SPE extraction (60% MEOH) (red trace) of the XAD-bound sample at 280 nm (a), 320 nm (b) and 370 nm (c) from Example 7.

An alternative approach, based on ethyl acetate extraction, was then used. The resulting HPLC traces (FIG. 12) exhibited a greater number of peaks at a significantly higher abundance and better resolution than the traces from the SPE clean-up. Thus, only the ethyl acetate extracts were used for the remainder of the study. Ethyl acetate extraction was carried out on both acidified and basified aqueous solutions of the samples to ensure that as many compounds as possible would be extracted from the samples.

Quantification of selected polyphenols: Initially, the levels of selected compounds, were quantitatively determined in both acidic and basic extracts of the three samples against methyl-4-formyl benzoate. However, this compound exhibited a strong matrix-related bias and thus the results obtained from its use were questionable. To eliminate such bias an external calibration curve of p-coumaric acid was established and was used to obtain quantitative results. Each compound was quantified based on its maximum UV absorbance in one of the three wavelengths (280, 320 or 370 nm). No response factors were determined for individual compounds and therefore the results of all compounds (apart from p-coumaric acid) are semi-quantitative in nature. The results obtained for the selected compounds are shown in FIG. 13. In the figure,

[a]samples were weighed in the form they were provided. No further treatment was applied prior to extraction.

[b]analyses were carried out with enhanced sample-size (~800 mg for MFP and ~1604 mg for sugar)

[c]trace=less than 0.1 mg/Kg

As can be seen, the XAD sample was by far the richest, among all three samples, in these phenolics. Also, the acidic XAD and MFP fractions contained a greater amount of polyphenolic compounds compared to the corresponding basic fractions. This was to be expected, considering that phenolic acids such as coumaric, ferulic and syringic acids have been reported previously as being the major phenolic constituents of sugarcane products. The sugar sample contained the lowest amount of polyphenolic compounds compared to the XAD and MFP samples. However, it was likely that many of the sugar polyphenolics were below the limit of detection of the HPLC method due to the higher content of sugar (per weight unit) in this sample compared with the XAD and MFP samples. To overcome this problem analyses with increased sample size were performed in order to detect additional compounds in the low GI sugar (acidic fraction only). Enhanced sample size analyses were also performed for the MFP sample to increase the number of compounds detected (acidic fraction only).

The presence/absence of selected compounds in some samples (due to time constraints) was confirmed by LC-MS studies (e.g. parent-product reactions, selected reaction monitoring and product-specific reactions). FIG. 14 summarises the LC-MS experiments performed for each sample and the information produced for each analyte. In the figure, [a]identification of tricin was based only on MS fragmentation as no authentic reference compound could be obtained and therefore is tentative.

Some compounds shown as 'not detected' in FIG. 13 were detected in some samples during various LC-MS experiments (e.g. apigenin in XAD-basic and MFP-basic, (−)-catechin gallate in MFP-acid and MFP-basic, luteolin in MFP-acid and MFP-basic). This is possibly due to the better sensitivity of the LC-MS system running in the selected-reaction-monitoring (SRM) mode compared to UV detection employed by the HPLC approach.

A series of LC-MS/MS experiments were carried out on the XAD-acid sample in an attempt to identify as many additional phenolic constituents possible within the timeframe given. Compounds mainly targeted included flavone glycosides previously found in sugarcane extracts, diosmetin (free aglycone of diosmin, already detected in the extracts) and glycosides containing aglycones already confirmed to be present in the extracts (apigenin, tricin, luteolin, quercetin). The results are summarised in Table 11 below. Several of the tentatively identified components have similar structures differing only in the nature of the substituent groups as illustrated by the structures below.

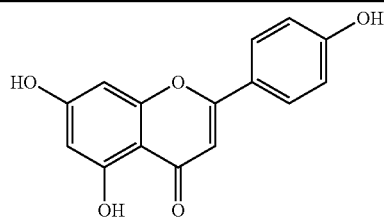

Apigenin

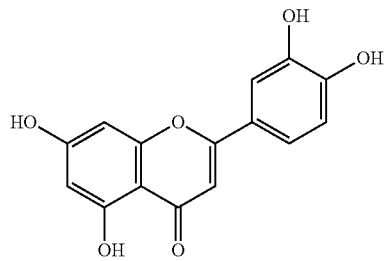

Luteolin

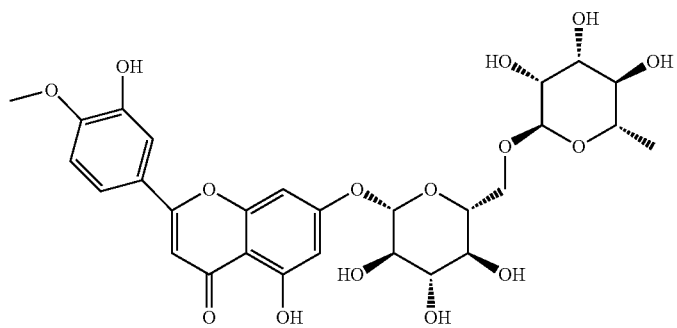

Diosmin

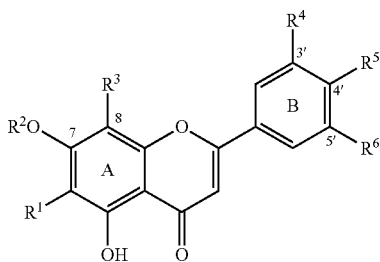

| | $R^1$ | $R^2$ | $R^3$ | $R^4$ | $R^5$ | $R^6$ |
|---|---|---|---|---|---|---|
| Tricin-7-O-neohesperoside | H | Glc-Rha | H | OCH$_3$ | OH | OCH$_3$ |
| Luteolin-8-C-(rhamnosylglucoside) | H | H | Glc-Rha | OH | OH | H |
| Tricin-7-O-glycoside | H | Glc-Rha | H | OCH$_3$ | OH | OCH$_3$ |
| Schaftoside | Glc | H | Ara | H | OH | H |
| Isoschaftoside | Ara | H | Glc | H | OH | H |

TABLE 11

List of compounds identified from LC-MS/MS experiments in the XAD-acid extract.

| Compounds | Detected in XAD-acid |
|---|---|
| Diosmetin | Yes |
| Myricetin | Yes |
| Tricin-7-O-neohesperidoside | Yes |
| Luteolin-8-C-(rhamnosylglucoside) | Yes |
| Vitexin | No |
| Tricin | Yes |
| Orientin | No |
| Tricin-7-O-glycoside | Yes |
| Schaftoside | Yes |
| Isoschaftoside | Yes |
| 4,5-Dimethyl-luteolin-8-C-glucoside | No |
| Luteolin/Kaempferol glycosides | No |
| Tricin glycosides | Yes |
| Apigenin glycosides | No |
| Diosmetin glycosides | Yes |
| Quercetin glycosides | No |

Figure 15:
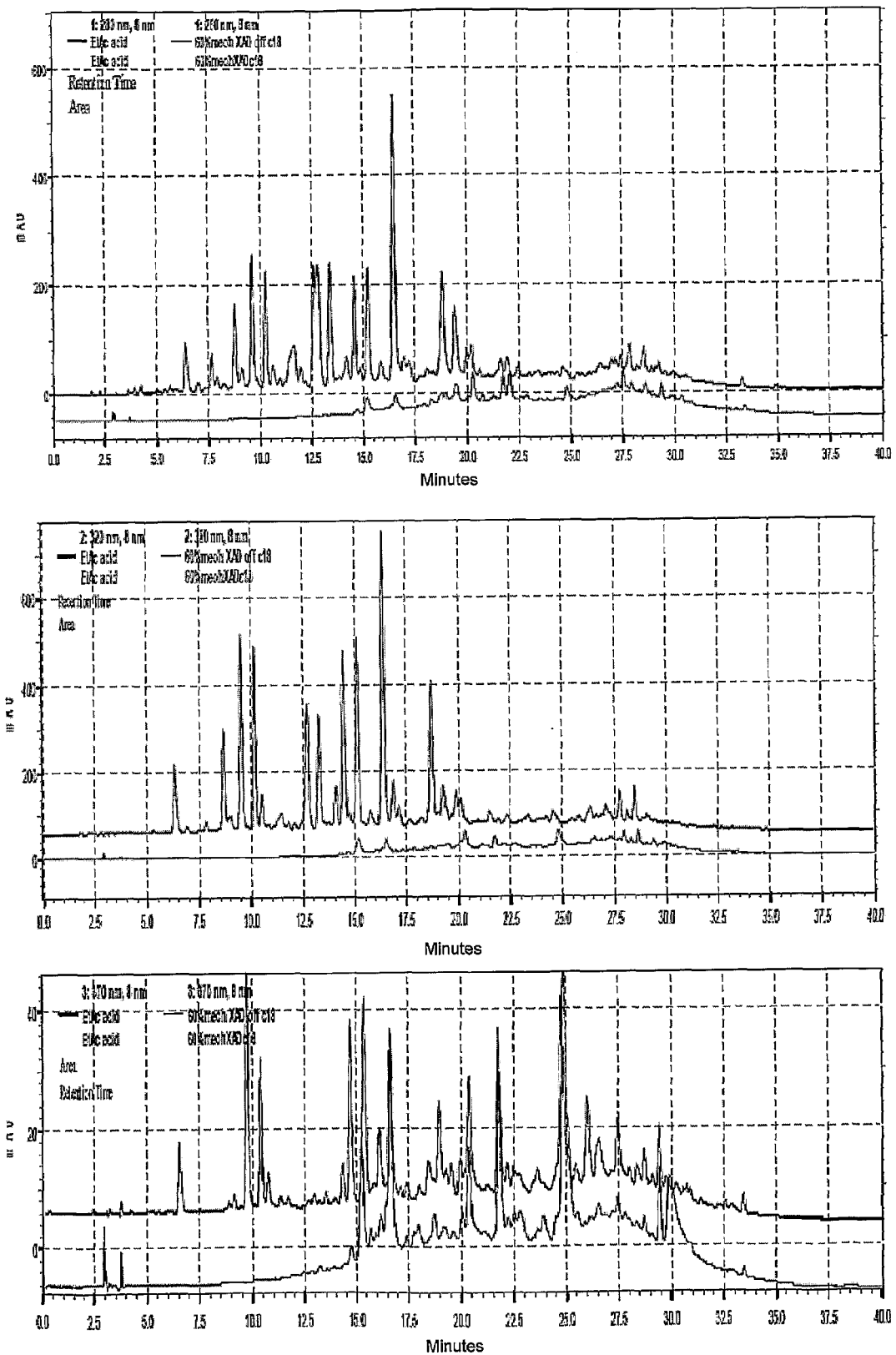
FIG. 15 shows the SRM and product-specific MS/MS ion chromatograms showing tricin and tricin-containing compounds detected in the XAD-acid extract from Example 7.
Figure 16:
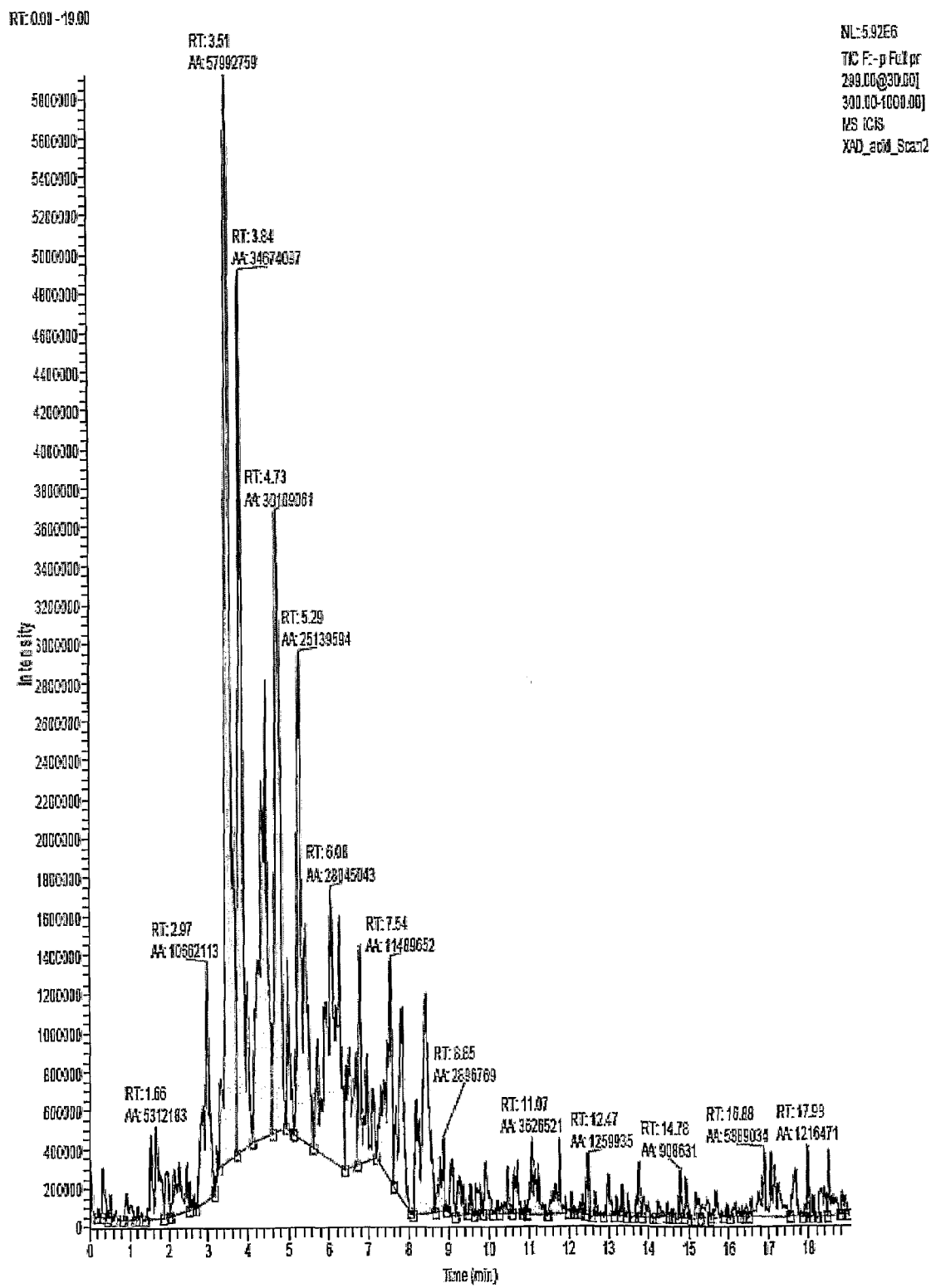
FIG. 16 shows the product-specific MS/MS ion chromatogram (parent m/z 299) showing several diosmetin-containing compounds in the XAD-acid extract from Example 7.

SRM and product-specific experiments highlighted the presence of additional (to those shown in Table 20) tricin-containing compounds in the XAD-acid extract (FIG. 15). However, it appears that diosmetin-containing compounds are the dominating group, at least in the XAD-acid extracts, as several of them were detected during product-specific (m/z 299) analysis (FIG. 16).

Conclusion

The HPLC and LCMS analysis of the XAD and MF powders from sugarcane showed that both contained a unique range of polyphenols and flavonoids quite different in level and mix to that found in other plant sources. They were also different to that found in extracts obtained by other methodology.

As expected the XAD powder had higher levels of the polyphenols compared to the MF powder. The general pattern of polyphenols found in the low GI sugar analysed was also similar to that found in the XAD and MF powders. This reinforced the use of the MF powder in the form of a high Brix syrup as an enrichment spray source to impregnate/coat refined or raw sugar crystals to deliver new functional ingredients with enhanced antioxidant activity and a favourable mineral balance.

These extracts can also be used to produce products having clinical benefits including influencing the GI of foods and modifying body composition. Such a syrup or powder could be used to enrich other food sources such as fibres and flours to deliver similar functional outcomes.

Example 8

A spray solution suitable for spraying onto raw sugar to convert it to a low GI sugar product was produced from the syrup from the 30 kDa membrane permeate (P1) of Example 1.

The permeate (P1) comprised approximately 4.5 g/l polyphenols, 30 g/l fructose, 30 g/l glucose and 110 g/l sucrose, having a Brix value of between 15 and 25.

The storage stability of the permeate was improved by evaporation to 60-70 BRIX, and approximately 4 fold increase in concentration. The composition was thus approximately 18 g/l polyphenols, 120 g/l fructose, 120 g/l glucose and 440 g/l sucrose.

This concentrated syrup was sprayed onto a base sugar. The base sugar consisted of (i) crystalline white sugar and (ii) in-process raw sugar from a primary mill or refinery at the fugal stage. The amount of spray solution varied depending upon the initial polyphenol/phytochemical content per kg of the base sugar. Typically between 1 to 12 ml of the concentrated spray syrup was added to each kg of base sugar—the exact amount depending upon the sugar cane variety being processed. For some varieties of cane sugar adequate phytochemical concentration could be achieved with minimal addition of spray syrup (depending upon the amount of reducing sugars remaining and phytochemical concentration). Following the fugal treatment the sugar was dried in a rotating cylindrical sugar drier and upon exit a sample was taken either on-line or off-line for quality assurance/quality control testing to ensure that an adequate polyphenol level is achieved.

A similar spraying procedure can be used to impregnate or coat white cane sugar, beet sugar and other carriers such as fibre (eg bagasse) and flour from various cereal sources in order to produce a bioactive enriched product for use as a functional food ingredient.

Example 9

Different processing streams were analysed during the production of raw sugar at a mill and in the case of molasses, compared with extracts prepared according to the ultrafiltration method of the present invention.

Samples: Samples were collected from the following processing streams: first extracted juice (FEJ), buffer tank (BT), mill mud filtrate (MMF), mill mud (MM), evaporator supply juice (ESJ), syrup (SYR), molasses (MOL) and raw sugar (RS). The samples were stored frozen and transported to the testing facility.

Sediment removal: Liquid samples (juices and mill mud filtrates) were centrifuged at 5000 rpm for 10 min at 5° C. and supernatants were vacuum filtered through Whatman No. 1 filter papers. Syrups, molasses and raw sugars were diluted to 10%, 10% and 40%, respectively, before sediment removal. Samples for mineral analysis were not treated to remove sediment.

Mill mud extracts: A mill mud extract was prepared by homogenising 20 g of mill mud for 1 min in 45 ml of hot (60° C.) deionised water, centrifuging at 5000 rpm for 5 min and decanting the supernatant. The pellet was re-extracted in 45 ml of hot deionised water and the supernatant again collected. The combined extracts were made up to 100 ml with deionised water and vacuum filtered through Whatman No. 1 filter papers.

Analyses: The following methods of analysis were used:

| Component | Method |
|---|---|
| Total phenolics | Folin-Ciocalteu colorimetric procedure. Results expressed as g catechin equivalents per 1. |
| Polyphenol profile | RP-HPLC, C18 column, (Luna 3 μm, Phenomenex) at 30° C., linear gradient 3-21% acetonitrile for 12 min, 21-60% for 1 min and 21-60% for 3 min. Detection at 214 nm. |
| Antioxidant activity | ABTS substrate. Results expressed as g gallic acid equivalents per 1. |
| Mono- and di-saccharides | RP-HPLC, NH2 column at 40° C., isocratic elution with 88% acetonitrile at 1 ml/min for 20 min. R I detection. |
| cis- and trans-aconitic acids | Ion-moderated partition HPLC, Aminex column HPX-87H (Bio-Rad). Isocratic elution with 0.004 M $H_2SO_4$ at 0.6 ml/min for 40 min at 30° C. UV detection. Samples diluted in water pre-injection. |
| Total solids | Vacuum oven at 70° C. for 16 h. |
| Density | Anton Paar density meter. Readings at 20° C. in g/ml. |
| Total nitrogen | Kjeldahl method using Foss Tecator digestion and distillation units. |
| Non-protein nitrogen | Sample (2.5 g) made to 50 ml with 12% trichloroacetic acid and filtered. Aliquot (20 ml) analysed by Kjeldahl method. |
| Fat | Acid hydrolysis followed by Mojonnier extraction. |
| Polysaccharides | Measurement of soluble polysaccharides (Roberts, 1981). Precipitation of polysaccharides with 100% ethanol, wash with 80% ethanol, digestion of precipitate in 1% sulphuric acid and measurement total reducing sugars by phenol-sulphuric acid at 485 nm with glucose as reference. Results expressed as g polysaccharide per 1. |
| Na, K, Ca, Mg, $PO_4$, $SO_4$ | Inductively coupled plasma - optical emission spectroscopy (ICP-OES) on Varian Vista Pro instrument at UQ. Elements were tested on undiluted, unfiltered samples |
| Cl | Automated colorimetric analyser (Seal AQ2), EPA Method (EPA-124-A) |

Extract

The molasses was extracted several times using the follow process steps according to the process of the invention:

(a) heating and diluting the molasses with water until the viscosity of the resulting solution is between 50 and 100 centipoise and between 30 and 50 Brix at a temperature of about 50° C.;

(b) centrifuging the diluent using a continuous desludging centrifuge with the supernatant being directly processed through a ceramic or stainless steel membrane (of 0.1 to 0.5 micron) using a pressure of 4 Bar, a flow rate of approximately 30 to 100 l/hour and at a temperature 35 to 50° C.;

(c) heating the solution of step (b) to 75° C. and then maintaining it in that temperature range for about 20 minutesuntil a precipitate of insoluble calcium and magnesium salts forms;

(d) separating the precipitate and large particulate matter from the solution produced in step (c) by passing the mixture through a ceramic or stainless steel membrane (of 0.1 to 0.5 micron) using a pressure of 4 Bar, a flow rate of 30 to 100 l/hour and at a temperature of 50° C., the retentate being discarded and the permeate being collected;

(e) treating the permeate collected from step (d) by passing it though a combination of spirally wound ultrafiltration membranes.

The ultrafiltration membranes were changed each time the process was run. The ultrafiltration membranes had size exclusion ranging from 1000 to 50,000 Dalton. The extracts thus isolated had the compositions set out in FIG. 25. In the figure, Perm=Permeate; Ret=Retentate and the data shows percentages of each molasses component in permeate and retentate.

Results

As illustrated by FIGS. 17 to 24, the composition of the different processing streams vary widely. Furthermore, the composition of the feed streams varies from batch to batch of sugar cane.

In the figures, the following abbreviations are used:
BT=Buffer tank
MMF=Mill mud filtrate
MM=Mill mud
MME=Mill mud extract (hot water extract, 20 g/100 ml total extract)
ESJ=Evaporator supply juice
SYR=Syrup
MOL=Molasses
RS=Raw sugar
FEJ=First extracted juice. (In FIG. 17, the sample is taken from Batch 3. No FEJ sample was provided for Batch 1 or Batch 2.)

Conclusion

These findings clearly demonstrate the partitioning of bioactive phytochemicals in primary mill sugar cane process streams. Such partitioning indicates that certain streams will be suited for different commercial exploitation of these phytochemicals.

Clarified juice, syrup, molasses and mill mud extracts are all potential sources as feedstocks for the recovery of bioactives such as polyphenols/antioxidants, organic acids and minerals. Molasses is the preferred source. Mill mud and bagasse are also useful sources of phytochemicals where a different composition is desired, especially one with higher levels of policosanols and phytosterols but lower levels of carbohydrates.

The five ultrafiltration extracts prepared from the molasses were each used as feed stock for further processing using XAD. The use of these extracts as feedstocks offers the clear benefit that they will minimize the chance of poisoning the XAD resins thus improving the efficiency and useable life of the resins.

Example 10

Three separate extraction processes were carried out as follows to prepare starting materials appropriate for use in the process according to the second aspect of the invention:
1. Fibrated cane tops were dried in a vacuum oven at 40° C. of one Group. The dried material was extracted with n-heptane using a soxhlet extractor of rabout 4 hours during which time at least 10 cycles were completed. The extract was dried over anhydrous sodium sulphate and evaporated to dryness to give an oily/waxy material in 1.2% yield, based on dry weight of cane tops.

2. Bagasse was treated in the same manner. The dried material gave an oily/waxy material in 0.65% yield, based on dry weight of bagasse.
3. Mill mud was treated in the same manner. The dried material gave an oil/waxy material in 6.53% yield, based on dry weight of mill mud.

The three extracts were then subjected to the process of Example 9 to provide three extracts according to the present invention. The extracts were high in polyphenols but low in sugars and would be useful for applications where sugars are not required.

The example also demonstrates that a range of feedstocks can be utilized in producing the extracts described as part of the invention.

Example 11

The method according to the second aspect of the invention was used to produce an extract according to the invention from biodunder.

TABLE 12

| Composition of biodunder extract | |
|---|---|
| Component | Biodunder |
| Total solids (g/100 g) | 10.4 |
| ° Brix | 11.4 |
| Density (g/ml) | 1.05 |
| Colour ($A_{420}$) | 17.8 |
| Conductivity (M NaCl equiv.) | 0.25 |
| pH | 4.1 |
| Total phenolics (g CE/l) | 6.2 |
| Antioxidant activity (g GAE/l) | 1.8 |
| Fructose (g/l) | 1 |
| Glucose (g/l) | 1 |
| Sucrose (g/l) | 3 |
| Ash g/100 g | 4 |

Conclusion

The extract produced in this example was high in polyphenols but low in sugars and would be useful for applications where sugars are not required. The example also demonstrates that biodunder is a useful feedstock for producing extracts according to the invention.

Example 12

This example demonstrates that molasses from a primary mill has a different composition from a refinery.

TABLE 13

| Composition of molasses from different sources | | |
|---|---|---|
| Component | Mill 1 (Primary Mill) | Mill 2 (Refinery) |
| Total solids (g/100 g) | 75.4 | 84.3 |
| Brix | 76 | 79 |
| Colour (ICU) A420 | 117 407 | 58 957 |
| Total phenolics (mg CE/100 g DW) | 2842 | 1258 |
| Antioxidant activity (mg GAE/100 g DW) | 864 | 373 |
| Fructose (g/100 g DW) | 9.7 | 5.2 |
| Glucose (g/100 g DW) | 6.0 | 5.2 |
| Sucrose (g/100 g DW) | 38.4 | 59.0 |

The example demonstrates that the source of molasses may vary and that this factor needs to be considered in producing the extracts according to the invention.

Example 13

In this example, the composition of mill mud was analysed to demonstrate its potential as a feedstock to prepare extracts according to the invention. The results are in FIG. 26.

The aqueous extracts produced in this example were high in polyphenols but low in sugars demonstrating that mill mud would be useful for producing extracts for applications where sugars are not required.

Example 14

The following table shows the differences in the extracts obtained using the method disclosed in international patent application no WO 2005/117608 compared with the extracts according to the present invention.

TABLE 14

| Composition of extracts made using different processes | | |
|---|---|---|
| Compound | WO 2005/117608 method | MF |
| Moisture (% wt/wt) | 2-5 | 3-6 |
| Sucrose (%) | 0.1-0.2 | 50-75 |
| Glucose (%) | 0.2-0.6 | 6-15 |
| Fructose (%) | 1.2-2.4 | 6-15 |
| Calcium (mg/g) | 6-8 | 3-4 |
| Magnesium (mg/g) | 2-3 | 1-5-3.0 |
| Potassium (mg/g) | 0.2-0.3 | 8-12 |
| Sodium (mg/g) | 0.05-0.07 | 1-2 |
| Polyphenols (mg CE/g) | 180-240 | 15-25 |
| Antioxidants (mg GAE/g) | 50-70 | 4-7 |
| Trans-aconitic acid (%) | 0-0.1 | 1.5-3.0 |
| Phosphate (mg/g) | n/d | 0.2-0.4 |
| Chloride (mg/g) | n/d | 1.8-2.5 |
| Sulphate (mg/g) | n/d | 10-15 |

It is important to note that molasses feedstocks vary significantly, particularly in mineral composition, as a result of the variability in the cane being processed and the processing conditions used (particularly in the liming and flocculation step to clarify the mixed juice).

The above table shows that the method according to the present invention produces an extract which has a very different composition to that of the extract disclosed in international patent application no WO 2005/117608. This difference is not simply the difference in the molasses feedstock used. The extract according to the invention has a much lower polyphenols content and a much higher content of the other phytochemicals which makes it closer to the natural composition of the sugar cane.

Example 15

This example compares the extract obtained from biodunder in Example 11 with pools 1 to 4 from Example 6.

TABLE 15

| Comparison of biodunder extract with different fractions of molasses extract Summary of Results, mg/Kg | | | | | |
|---|---|---|---|---|---|
| Target Compounds | Biodunder | Pool 1 | Pool 2 | Pool 3 | Pool 4 |
| Cinnamic Acid | 473.60 | | | 2.5 | 16.9 |
| Epicatechin | | 3.1 | 6.1 | 69.1 | 268.2 |

TABLE 15-continued

Comparison of biodunder extract with different
fractions of molasses extract
Summary of Results, mg/Kg

| Target Compounds | Biodunder | Pool 1 | Pool 2 | Pool 3 | Pool 4 |
|---|---|---|---|---|---|
| Gallic Acid | | | | 6.3 | |
| Myrcetin | 23.7 | | | 1.0 | 62.9 |
| Protocatechoic Acid | | 15.2 | 8.0 | | |
| Syringic Acid | 58.0 | 2.7 | 6.1 | 68.3 | 261.9 |
| Vanillic Acid | 176.0 | | 4.6 | 8.5 | 81.8 |
| Vanillin | | 5.4 | | 7.5 | 6.3 |
| Para-hydroxy Benzoic Acid | | | 3.7 | | 28.3 |
| p-Coumaric Acid | | 5.0 | | | |
| Apigenin | 29.5 | | | | |
| Caffeic Acid | | | 0.8 | 3.1 | |
| Diosmin | 19.0 | | | | |
| Ferulic Acid | | | | | 4.7 |
| Kaempferol | 88.0 | | | | |

The word 'comprising' and forms of the word 'comprising' as used in this description and in the claims does not limit the invention claimed to exclude any variants or additions.

Modifications and improvements to the invention will be readily apparent to those skilled in the art. Such modifications and improvements are intended to be within the scope of this invention.

The claims defining the invention are as follows:

1. A process for producing a polyphenol-containing extract from a sugar cane product, the process comprising:
   (a) combining the sugar cane product and an aqueous solution to yield a mixture having a Brix value not greater than about 50 Brix;
   (b) heating a diluted mixture from step (a) until a precipitate of insoluble calcium and magnesium salts forms;
   (c) passing the mixture produced in step (b) through a ceramic or stainless steel membrane with a pore size between 0.1 and 0.5 micron and retaining the mixture that permeates the membrane;
   (d) passing the permeate from step (c) through, a 30 to 100 Kda ultrafiltration membrane; and
   (e) retaining the mixture that permeates the membrane, wherein the permeate of step (e) comprises one or more polyphenols, one or more carbohydrates, one or more minerals and one or more organic acids, and wherein the sugar cane product is selected from the group consisting of molasses, dunder, bagasse and mixtures thereof.

2. The process according to claim 1, wherein the sugar cane product is bagasse.

3. The process according to claim 1, wherein the sugar cane product is molasses.

4. The process according to claim 1, wherein the sugar cane product is dunder.

5. The process according to claim 1, further comprising heating the mixture to a temperature such that the viscosity of the mixture is not greater than about 100 centipoise.

6. The process according to claim 1, wherein in step (b) the temperature of the mixture is brought to about 50° C. prior to removing particulate matter therefrom.

7. The process according to claim 1, wherein the ultrafiltration membrane has a size exclusion in the range from 50 kDa to 30 kDa.

8. The process according to claim 7, wherein the ultrafiltration membrane has a size exclusion of 30 kDa.

9. The process according to claim 1, wherein the polyphenol-containing extract is a powder.

10. The process according to claim 1, wherein the diluted product from step (a) is heated to a temperature in a range of from 70 to 80° C. and maintained at a temperature in a range of from 70 to 80° C. for a period of time until the precipitate of insoluble calcium and magnesium salts forms.

11. The process according to claim 1, wherein the polyphenol-containing extract is a powder comprising 1.5 to 2.5 wt% of one or more polyphenols.

12. The process according to claim 1, wherein the polyphenol-containing extract is a syrup comprising 3.5 to 6 g CE/l of one or more polyphenols.

* * * * *